United States Patent
Klein et al.

(10) Patent No.: US 6,441,053 B1
(45) Date of Patent: Aug. 27, 2002

(54) INHIBITORS OF GLYCOGEN SYNTHASE KINASE-3 AND METHODS FOR IDENTIFYING AND USING THE SAME

(75) Inventors: Peter S. Klein, Wynnewood, PA (US); Douglas Melton, Lexington, MA (US)

(73) Assignees: The Trustees of the University of Pennsylvania, Philadelphia, PA (US); President and Fellows of Harvard University, Cambridge, MA (US)

(*) Notice: Subject to any disclaimer, the term of this patent is extended or adjusted under 35 U.S.C. 154(b) by 0 days.

(21) Appl. No.: 09/327,660

(22) Filed: Jun. 8, 1999

Related U.S. Application Data

(62) Division of application No. 08/846,914, filed on Apr. 30, 1997.
(60) Provisional application No. 60/016,990, filed on May 7, 1996.

(51) Int. Cl.$^7$ .................. A61K 47/00; A61K 31/33; A61K 31/55; A61K 31/40; C12Q 1/48

(52) U.S. Cl. .................. 514/789; 424/610; 514/211; 514/410; 514/183; 435/15

(58) Field of Search .................. 424/610; 514/211, 514/410, 183, 789; 435/15

(56) References Cited

U.S. PATENT DOCUMENTS

| | | | |
|---|---|---|---|
| 2,202,325 A | 5/1940 | Warburton | 167/75 |
| 5,843,935 A | * 12/1998 | Heath, Jr. et al. | 514/183 |
| 5,945,440 A | * 8/1999 | Kleinschroth et al. | 514/410 |
| 6,057,117 A | * 5/2000 | Harrison et al. | 435/7.93 |

FOREIGN PATENT DOCUMENTS

WO 94/02488 * 2/1994

OTHER PUBLICATIONS

Ahlgren, S.C. et al., "Protein Kinase C Inhibitors Decrease Hyperalgesia and C–Fiber Hyperexcitability in the Streptoxotocin–Diabetic Rat", J. Neurophysiology 72(2): 684–692, Aug. 1994.*
Nabeshima, T. et al., "Staurosporine Facilitates Recovery from the Basal Forebrain–Lesion–Induced Impairment of Learning and Deficit of Cholinergic Neuron in Rats,", J. Pharm. Exp. Ther. 257(2): 562–566, May 1991.*
Bradshaw, D. et al. "Therapeutic Potential of Protein Kinase C Inhibitors", Agents Actions 38: 135–147, Aug. 1994.*
Abate et al., 1990, Mol. Biol. 10:5532–5535.
Anderson et al., 1982, Electrophoresis 3:135–142.
Angel et al., "Oncogene jun encodes a sequence–specific trans–activator similar t AP–1", 1988, Nature 332:166–171.
Angel et al., "The jun Proto–oncogene is positively auto–regulated by its product, Jun./AP–1", 1988, Cell, 55:875–885.
Angel et al., "The role of Jun, Fos and the AP–1 complex in cell–proliferation and transformation", 1991, Biochim. Biophys. Acta, 1072:129–157.
Atack et al., "Effects of L–690, 488, a Prodrug of the Bisphosphonate Inositol Monophosphatase Inhibitor L–690, 330, on Phosphatidylinositol", 1994, J. Pharmacol., Exp. Ther. 270:70–76.
Atack et al., "In vitro and in vivo inhibition of Inositol Monophosphatase by the Bisphosphonate L–690, 330", 1993, J. Neurochem. 60:652–658.
Avissar et al., "Lithium inhibits adrenergic and cholinergic increases in GTP binding in rat cortex", 1988, Nature 331:440–442.
Baraban, 1994, "Toward a crystal–clear view of lithium's site of action", Proc. Natl. Acad. Sci. U.S.A. 91:5738–5739.
Behrens et al., "Functional interaction of β–catenin with the transcription factor LEF–1", 1996, Nature 382:638.
Berridge et al., "Changes in the levels of inositol phosphates after agonist–dependent hydrolysis of membrane phosphoinositides", 1983, Biochem J. 212:473–482.
Breckenridge et al., "Lithium inhibits morphogenesis of the nervous system but not neuronal differentiation in *Xenopus laevis*", 1987, Development 99:353–370.
Bunney, et al., 1987, In: Psychopharmacology: The Third Generation of Progress, Hy.ed., New York, Raven Press, 553–565.
Berridge et al., "Neural and Developmental Actions of Lithium: A unifying Hopothesis", 1989, Cell 59:411–419.
Bohmann et al., "Biochemical analysis of transcriptional activation by Jun: differential acitvity of c– and v–Jun", 1989, Cell 59:709–717.
Bosch et al., "Effects of Lithium Ions on Glycogen Synthase and Phosphorylase in Rat Hepatocytes", 1986, J. Biol. Chem. 261:16927–16931.
Busa et al., "Lithium–induced Teratogenesis in Frog Embryos Prevented by a Polyphosphoinositide Cycle Intermediate or a Diaglycerol Analog", 1989, Dev. Biol. 132:315–324.
Chiu et al., "The c–Fos protein interacts with Jun/AP–1 to stimulate transcription of AP–1 responsive genes", 1988, Cell 54:541–552.
Cohen et al., "Separation and characterisationof glycogen synthase kinase 3, glycogen synthase 4 and glycogen kinase 5 from rabbit skeletal muscle", 1982, Eur. J. Biochem. 124:21–35.

(List continued on next page.)

*Primary Examiner*—Rebecca E. Prouty
(74) *Attorney, Agent, or Firm*—Morgan, Lewis & Bockius, LLP

(57) ABSTRACT

A method of identifying inhibitors of glycogen synthase kinase-3 is provided. The method comprises providing a mixture comprising GSK-3, a phosphate source, and a GSK-3 substrate, incubating the mixture in the presence or absence of a test compound, and assessing the activity of GSK-3 in the mixture. A reduction of GSK-3 activity following incubation of the mixture in the presence of the test compound is an indication that the test compound is an inhibitor of GSK-3.

1 Claim, 10 Drawing Sheets

OTHER PUBLICATIONS

Cook et al., "Wingless inactivates glycogen synthase kinase–3 via an intracellular signaling pathway which involves a protein kinase C", 1996, EMBO J. 15:4526–4536.

Davies et al., "Induction of Early Stages of Kidney Tubule Differentiation by Lithium Ions", 1995, Dev. Biol. 167:50–60.

Dent et al., "Multisite phoshorylation of the glycogen–binding subunit of protein phosphate–$I_G$ by cyclic AMP–dependent protein kinase and glycogen synthase kinase–3", 1989, FEBS Lett. 248:67–72.

Dominguez et al., "Role of glycogen synthase kinase 3β as a negative regulator of dorsoventral axis formation in Xenopus embryos", 1995, Proc. Natl. Acad. Sci. U.S.A. 92:8498–8502.

Dong et al., "AP–1/Jun is required for early Xenopus development and mediates mesoderm induction by fibroblast growth factor but not by activin", 1996, J. Biol. Chem. 271:9942–9946.

Doukas et al., 1986, Exp. Hematol. 14:215–221.

Drayer et al., "role of phospholipase C in Dictyostelium: formation of inositol 1,4,5–trisphosphate and normal development in cells lacking phospholipase C activity", 1994, EMBO J. 13:1601–1609.

Embi, et al., 1980, Eur. J. Bichem., 107:519–527.

Fagotto et al., "β–catenin localization during xenopus embryogenesis: accumulation at tissue and somite boundaries", 1994, Development 120:3667–3679.

Fiol et al., "Formation of Protein Kinase Recognition Sites by Covalent Modification of the Substrate", 1987, J. Biol. Chem. 262:14042–14048.

Fiol et al., "Ordered Multisite Protein Phosphorylation", 1990, J. B. Chem. 265:6061–6065.

Funayama et al., "Embryonic Axis Induction by the Armadillo repeat Domain β–catenin: Evidence for intracellular signaling", 1995, J. Cell Biol., 128:959–968.

Goedert et al., "Expression of separate isoforms of human tau protein: correlation with the tau pattern in brain and effects on tubulin polymerization", 1990, EMBO J. 9:4225–4230.

Hallcher et al., "The effects of lithium ion and other agents on the activity of myo–Inositol–1–phosphatase from Bovine Brain", 1980, J. Biol. Chem. 255:10896–10901.

Hammond et al., "Lithium Therapy of Canine Cyclic Hematopoiesis", 1980, Blood 55:26–28.

Hanger et al., "Glycogen synthase kinase–3 induces Alzheimer's disease–like phosphorylation of tau: generation of paired helical filament epitopes and neuronal locatisation of the kinase", 1992, Neurosci. Lett. 147:58–62.

Harwood et al., "Clycogen Synthase Kinase 3 Regulates Cell Fate in Dictyostelium", 1995, Cell 80:139–148.

He et al., "Glycogen Synthase Kinase–3 and Dorsoventral Patterning in Xenopus Embryos", 1995, Nature 374:617–622.

Heasman et al., "Overexpression of Cadherins and Underexpression of β–Catenin inhibit dorsal mesodern induction in early xenopus embryos", 1994, Cell 79:791–803.

Hedgepeth et al., "Activation of the Wnt Signaling Pathway: A Molecular Mechanism for Lithium Action", 1997, 185:001–0010.

Hemmings et al., "Purification of Glycogen Kinase 3 from Rabbit Skeletal Muscle", 1982, Eur. J. Biochem. 119:443–451.

Hemmings et al., "Reconstruction of a Mg–ATP–dependent protein phosphatase and its activation through a phosphorylation mechanism", 1982, FEBS Lett. 150:319–324.

Herzlinger et al., Induction of Kidney Epithelial Morphogenesis by Cells Expressing Wnt–1, 1994, Dev. Biol. 166:815–818.

Hunter et al., "The protein kinases of budding yeast: six score and more", 1997, TIBS 22:18–22.

Jefferson et al., 1989, In: Comprehensive Textbood of Psychiatry, Kaplan et al., eds., Williams & Wilkins, Baltimore, 2:1655–1662.

Jope et al., "Lithium and Brain Signal Transduction Systems", 1994, Biochem. Pharmacol. 47:429–441.

Kao et al., "Lithium–induced respecification of pattern in *Xenopus laevis* embryos", 1986, Nature 322:371–373.

Klein et al., "A molecular mechanism for the effect of lithium on development", 1996, Proc. Natl. Acad. Sci. U.S.A., 93:8455–8459.

Korinek et al., "Constitutive Transcriptional Activation by a β–Catenin–Tcf Complex in $APC^{-/-}$ Colon Carcinoma", 1997, Science 275:1784–1787.

Kosik et al., 19988, Neuron, 7:817–825.

Laemmli et al., "Cleavage of Structural Proteins during the Assembly of the Head of Bacteriophage T4", 1970, Nature 227:680–685.

Lee, "Disruption of the cytoskeleton in Alzheimer's disease", 1995, Curr. Op. Neurobiol. 5:663–668.

Livingston et al., "Lithium evokes expression of vegetal–specific molecules in the animal blastomers of sea urchin embryos", 1989. Proc. Natl. Acad. Sci. U.S.A 86:3669–3673.

Lovestone et al., "Alzheimer's disease–like phosphorylation of the micro–tubule–associated protein tau by glycogen synthase kinase–3 in transfected mammalian cells", 1994, Curr. Biol. 4:1077–1086.

Maeda, "Influence of ionic conditions on cell differentiation and morphogenesis of the cellular slime molds", 1970, Dev. Growth and Differ. 12:217–227.

Mandelkow et al., "Glycogen synthase kinase–3 and the Alzheimer–like state of microtubule–associated protein tau", 1992, FEBS Lett. 314:315–321.

Mandelkow et al., "Tau as a marker for Alzheimer's disease", 1994, Trends Biol. Sci. 18:480–483.

Manji et al., "Signal Transduction Pathways", 1995, Arch. Gen. Psychiatry 52:531–543.

McMahon et al., "Ectopic expression of the proto–oncogene int–1 in xenopus embryos leads to duplication of the embryonic axis", 1989, Cell 58:1075–1084.

Shen et al., "Effects of Lithium and Haloperidol on human sperm motility in–vitro", J. Pharm. Pharmacol., 1992, 44:534–536.

Miller et al., "Signal transduction through β–catenin and specification of cell fate during embryogenesis", 1996, Genes & Dev. 10:2527–2539.

Molenaar et al., "XTcf–2 transcription factor mediates β–catenin–induced axis formation in xenopus embryos", 1996, Cell 86:391–399.

Moon et al., "Structurally Related Receptors and Antagonists Compete for Secreted Wnt Ligands", 1997, *Cell*, 68:725–728.

Mulot et al., "PHF–tau from Alzheimer's brain comprises four species on SDS–PAGE which can be mimicked by in vitro phosphorylation of human brain tau by glycogen synthase kinase–3β", 1994, FEBS Lett., 349:359–364.

Ng et al., "Effect of protein kinase C modulators on the leucocyte Na$^+$/H$^+$ antiport in Type 1 (insulin–dependent) diabetic subjects with albuminuria", Diabetologia, 1990, 33:278–284.

Nikolakaki et al., Glycogen synthase kinase 3 phosphorylates Jun family members in vitro and negatively regulates their transactivating potential in intact cells, 1993, 8:833–840.

Nusse et al., "Mode of proviral activation of a putative mammary oncogene (int–1) on mouse chromosome 15", 1984, Nature 307:131–136.

Otvos et al., "Monoclonal antibody PHF–1 recognizes tau protein phosphorylated at serine residue 396 and 404", 1994, J. Neurosci. Res. 39:669–673.

Peifer et al., Wingless signal and Zeste–white 3 kinase trigger opposing changes in the intracellular distribution of Armadillo, 1994, Dev., 120:369–380.

Perrimon, "Serpentine Proteins Slithe into the Wingless and Hedgehog Fields", 1996, Cell 86:513–516.

Perrimon, "The genetic basis of patterned baldness in drosophila", 1994, Cell 76:781–784.

Physicians Desk Reference, 51st Ed., 1997, pp. 2352, 2658.

Pierce et al., "Regulation of Spemann organizer formation by the intracellular kinase Xgsk–3", 1995, Development 121:755–765.

Plyte et al., "Glycogen synthase kinase–3: functions in oncogenesis and development", 1992, Biochim. Biophys. Acta 1114:147–162.

Price et al., "Lithium in the Treatment of Mood Disorders", 1994, New Eng. J. Med. 331:591–598.

Ptashne et al., 1980, J. Cell Physiol. 103:41–46.

Quesenberry et al., "Lithium Stimulation of Murine Hematopoiesis in Liquid Culture: An effect mediated by marrow stromal cells", 1984, Blood 63:121–127.

Ramakrishna et al., 1989, Biochem. 28:856–860.

Ramakrishna et al., 1985, J. Biol. Chem. 260:12280–12286.

Risby et al., 1991, Arch. Gen. Physchiatry 48:513–524.

Rotem et al., "Protein kinase C is present in human sperm: Possible role in flagellar motility", Proc. Natl. Acad. Sci. USA, 1990, 87:7305–7308.

Rubinfeld et al., "Stabilization of β–Catenin by Genetic Defects in Melanoma Cell Lines", 1997, *Science*, 1275:1790–1792.

Sassone–Corsi, "Transcriptional autoregulation of the proto–oncogene fos", 1988, Nature 334:314–319.

Schneider et al., "β–cantenin translocation into nuclei demarcates the dorsalizing centers in frog and fish embryos", 1996, Mech. Dev., 57:191–198.

Schonthal et al., 1988, Cell 54:325–334.

Siegfried et al., "Components of wingless signaling in drosophila", 1994, Nature 367:76–80.

Smith et al., 1983, Principles of Biochemistry, McGraw–Hill, New York, 194–198.

Stambolic et al., "Lithium inhibits glycogen synthase kinase–3 activity and mimics Wingless signaling in intact cells", 1996, Curr. Biol. 6:1664–1668.

Stachel et al., "Lithium perturbation and goosecoid expression identify a dorsal specification pathway In the pregastrula zebrafish", 1993, Development 117:1261–1274.

Stark et al., "Epithelial transformation of metanephric mesenchyme int eh developing kindey regulated by Wnt–4", 1994, Nature 372:679–683.

Stokoe et al., "MAPKAP kinase–2; a novel protein kinase activated by mitogen–activated protein kinase", 1992, EMBO J. 11:3985–3994.

Sutherland et al., "The α–isoform of glycogen synthase kinase–3 from rabbit skeletal muscle is inactivated by p70 S6 kinase or MAP kinase–activated protein kinase–1 invitro", 1994, FEBS Lett. 338:37–42.

Towbin et al., 1979, Proc. Natl. Acad. Sci. U.S.A. 76:4350–4354.

Turner et al., "Expression of achaete–scute homolog 3 in Xenopus embryos converts ectodermal cells to a neural fate", 1994, Genes & Dev. 8:1434–1447.

van Leeuwen, et al., "Biological activity of soluble wingless protein in cultured *Drosophila imaginal* disc cells", 1994, Nature 368:342–344.

Van Lookeren Campagne et al., "Lithium Respecifies Cyclic AMP–Induced Cell–Type Specific Gene Expression in Dictyostelium", 1988, Dev. Genet. 9:589–596.

Vandenheede et al., 1980, J. Biol. Chem. 255:11768–11774.

Wang, et al., "Liver Isozyne of Rabbit Glycogen Synthase", 1986, J. Biol. Chem. 261:16909–16915.

Wang, et al., "Isoform Differences in Substrate Recognition by Glycogen Synthase Kinases 3β in the Phosphorylation of Phosphatase Inhibitor 2†", 1993, Biochemistry 33:143–147.

Wang, et al., "Glycogen synthase kinase–3β is a dual specificity kinase differentially regulated by tyrosine and serine/threonine phosphorylation", 1994, J. Biol. Chem. 269:14566–14574.

Welsh et al., Research Communication: Glycogen synthase kinase–3 is rapidly inactivated in response to insulin and phosphorylates eukaryotic initiation factor elF–2B∈, 1993, Biochem. J. 294;625–629.

Wood et al., 1987, Psychol. Med. 17:570–600.

Woodgett, "A common denominator linking glycogen metabolism, nuclear oncogenes and development", 1991, Trends Biochem. Sci. 16:177–181.

Woodgett, 1990, EMBO J. 9:2432–2438.

Yost et al., "The axis–inducing activity, stability, and subcellular distribution of β–catenin is regulated in Xenopus embryos by glycogen synthase kinase 3", 1996, Genes & Dev., 10:1443–1454.

Boyle et al., "Activation of Protein Kinase C Decreases Phosphorylation of c–Jun at Sites That Negatively Regulate Its DNA–Binding Activity", 1991, Cell 64:573–584.

Smith et al., "OOgenesis and OOcyte Isolation", 1994, Methods Cell Biol., 36:45–58.

Sperber et al., "Glycogen synthase kinase–eβ phosphorylates tau protein at multiple sites in intact cells", 1995, Neurosci Lett. 197:149–153.

Sutherland et al., "Inactivation of glycogen synthase kinase 3β by phosphorylation: new kinase connections in insulin and growth–factor signalling", 1993, Biochem. J. 296:15–19.

Hegazy et al., "Inhibition of Glycogen Synthase Kinase 3 by polycations"FASEB J. 1988, 2:A596.

* cited by examiner

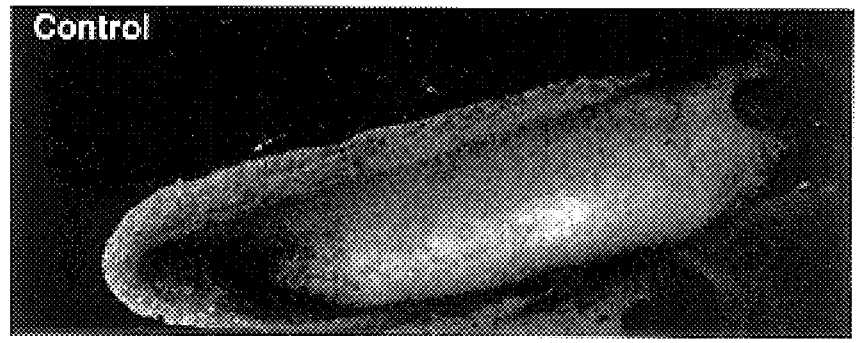
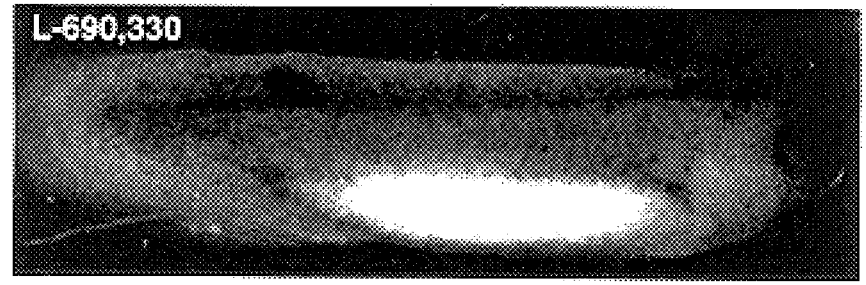
FIG.1C

DN-GSK-3

DN-GSK-3 + myo-inositol

INHIBITORS OF GLYCOGEN SYNTHASE KINASE-3 AND METHODS FOR IDENTIFYING AND USING THE SAME

CROSS REFERENCE TO RELATED APPLICATIONS

This application division of U.S. application Ser. No. 08/846,914, which was filed on Apr. 30, 1997 and which claims priority under 35 U.S.C. §119(e) to U.S. Provisional Application No. 60/016,990, filed on May 7, 1996.

FIELD OF THE INVENTION

The field of the invention is protein kinase enzymes involved in glycogen metabolism, in signal transduction, and in cellular regulation of enzyme activity and transcription.

BACKGROUND OF THE INVENTION

Lithium is an effective drug for the treatment of bipolar (manic-depressive) disorder (Price et al., 1994, New Eng. J. Med. 331:591–598; Goodwin et al., 1990, In: Manic-Depressive Illness, New York: Oxford University Press). Lithium is not only effective for treatment of acute episodes of mania, but this compound also reduces the frequency and severity of recurrent episodes of mania and depression in patients with bipolar and unipolar disorders (Goodwin, et al., 1990, supra). Lithium can be used to treat profound depression in some cases. Despite the remarkable efficacy of lithium observed during decades of its use, the molecular mechanism(s) underlying its therapeutic actions have not been fully elucidated (Bunney, et al., 1987, In: Psychopharmacology: The Third Generation of Progress, Hy, ed., New York, Raven Press, 553–565; Jope et al., 1994, Biochem. Pharmacol. 47:429–441; Risby et al., 1991, Arch. Gen. Psychiatry 48:513–524; Wood et al., 1987, Psychol. Med. 17:570–600).

Lithium does not have an immediate effect during the treatment of mania, but rather requires several weeks to manifest a clinical response. It has been suggested that this delay reflects changes in the expression of genes involved in alleviation of mania (Manji et al., 1995, Arch. Gen. Psychiatry 52:531–543).

In addition to its use as a therapeutic drug for the treatment of mania, lithium exhibits numerous physiological effects in animals. For example, lithium mimics insulin action by stimulating glycogen synthesis (Bosch et al., 1986, J. Biol. Chem. 261:16927–16931). Further, exposure to lithium has dramatic morphogenic effects during the early development of numerous organisms. The effects of lithium on the development of diverse organisms, including Dictyostelium, sea urchins, zebrafish, and Xenopus have been reported (Maeda, 1970, Dev. Growth & Differ. 12:217–227; Van Lookeren Campagne et al., 1988, Dev. Genet. 9:589–596; Kao et al., 1986, Nature 322:371–373; Stachel et al., 1993, Development 117:1261–1274; Livingston et al., 1989. Proc. Natl. Acad. Sci. U.S.A. 86:3669–3673). In Dictyostelium discoideum, lithium alters cell fate by blocking spore cell development and promoting stalk cell development (Maeda, 1970, supra; Van Lookeren Campagne et al., 1988, supra). In Xenopus, lithium induces an expansion of dorsal mesoderm, leading to duplication of the dorsal axis or, in extreme cases, entirely dorsalized embryos which lack identifiably ventral tissues (Kao et al., 1986, Nature 322:371–373). Lithium also rescues UV-ventralized embryos (Kao et al., 1986, supra). In addition, treatment of sea urchin animal blastomeres with lithium induces the blastomeres to display a morphology resembling that of isolated vegetal blastomeres (Horstadius, 1973, In: Experimental Embryology of Echinoderms, Oxford University Press, Oxford).

Even though lithium is remarkably effective for the treatment of mania in many human patients, lithium treatment in humans is accompanied by several serious drawbacks (Baraban, 1994, Proc. Natl. Acad. Sci. U.S.A. 91:5738–5739). Particularly troublesome is the slim margin between therapeutic and toxic levels of lithium in vivo. Furthermore, because clearance of lithium is intimately tied to sodium and water excretion, a slight change in electrolyte balance can precipitate a life-threatening increase in lithium levels in vivo (Baraban, supra). In addition, even tight regulation of lithium within its therapeutic window is associated with a wide range of side effects, such as tremor, renal dysfunction, thyroid abnormalities, and birth defects (Jefferson et al., 1989, In: Comprehensive Textbook of Psychiatry, Kaplan et al., eds., Williams & Wilkins, Baltimore, vol. 2, 1655–1662). It is recommended that facilities for prompt and accurate serum lithium determinations be available before administering lithium to a patient (Physicians Desk Reference, 51 st Ed., 1997, p. 2658). In addition, lithium should generally not be administered to patients having significant renal or cardiovascular disease, severe debilitation or dehydration, sodium depletion, or to patients receiving diuretics, since the risk of lithium toxicity is very high in such patients (Physicians Desk Reference, 1997, supra, at 2352). Numerous other side effects are detailed in the Physicians Desk Reference (1997, supra, at 2352, 2658).

The mechanism or mechanisms by which lithium exerts these diverse effects are unclear (Price et al., 1994, New Eng. J. Med. 331:591–598; Goodwin et al., 1990, In: Manic-Depressive Illness, New York, Oxford University Press; Berridge et al., 1989, Cell 59:411–419; Avissar et al., 1988, Nature 331:440–442). A favored hypothesis, the inositol depletion hypothesis, is based on the observation that lithium inhibits inositol monophosphatase (IMPase) and, by doing so, depletes cells of endogenous inositol (Berridge et al., 1989, Cell 59:411–419; Hallcher et al., 1980, J. Biol. Chem. 255:10896–10901). Cells that do not have an exogenous source of inositol would, in principle, be unable to synthesize phosphatidyl-3-inositol phosphate, the precursor of inositol 1,4,5 tris-phosphate ($IP_3$). Thus, according to the inositol depletion hypothesis, lithium-treated cells are unable to generate $IP_3$ in response to extracellular signals and, as a consequence, $IP_3$-dependent responses are blocked. Some experimental results appear to support the inositol depletion hypothesis (Baraban, 1994, Proc. Natl. Acad. Sci. U.S.A. 91:5738–5739; Berridge et al., 1989, Cell 59:411–419; Manji et al., 1995, Arch. Gen. Psychiatry 52:531–543; Busa et al., 1989, Dev. Biol. 132:315–324). However, other experimental results do not support this hypothesis (Klein et al., 1996, Proc. Natl. Acad. Sci. U.S.A., 93:8455–8459; Drayer et al., 1994, EMBO J. 13:1601–1609).

Glycogen synthase kinase-3 (GSK-3) is a serine/threonine protein kinase having a 47 kDa monomeric structure. It is one of several protein kinases which phosphorylates glycogen synthase (Embi, et al., 1980, Eur. J. Biochem., 107:519–527; Hemmings et al., 1982, Eur. J. Biochem. 119:443–451). GSK-3 is also referred to in the literature as factor A ($F_A$) in the context of its ability to phosphorylate $F_C$, a protein phosphatase (Vandenheede et al., 1980, J. Biol. Chem. 255:11768–11774). Other names for GSK-3 and homologs thereof include zeste-white3/shaggy (zw3/sgg; the *Drosophila melanogaster* homolog), ATP-citrate lyase kinase (ACLK or MFPK; Ramakrishna et al., 1989, Biochem. 28:856–860; Ramakrishna et al., 1985, J. Biol. Chem. 260:12280–12286), GSLA (the Dictyostelium homolog; Harwood et al., 1995, Cell 80:139–48), and MDSI, MCK1, and others (yeast homologs; Hunter et al., 1997, TIBS 22:18–22).

The gene encoding GSK-3 is highly conserved across diverse phyla. GSK-3 exists in two isoforms in vertebrates, GSK-3α and GSK-3β. In vertebrates, the amino acid identity among homologs is in excess of 98% within the catalytic domain of GSK-3 (Plyte et al., 1992, Biochim. Biophys. Acta 1114:147–162). It has been reported that there is only one form of GSK-3 in invertebrates, which appears to more closely resemble GSK-3β than GSK-3α. Amino acid similarities (allowing for conservative replacements) between the slime mold and fission yeast proteins with the catalytic domain of human GSK-3β are 81% and 78%, respectively (Plyte et al., 1992, supra). The remarkably high degree of conservation across the phylogenetic spectrum suggests a fundamental role for GSK-3 in cellular processes.

GSK-3 has been demonstrated to phosphorylate numerous proteins in vitro, including, but not limited to glycogen synthase, phosphatase inhibitor I-2, the type-II subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-myc transcription factor, adenomatous polyposis coli tumor suppressor protein, τ protein, and β-catenin (Plyte et al., 1992, Biochim. Biophys. Acta 1114:147–162; Korinek et al., 1997, Science 275:1784–1787; Miller et al., 1996, Genes & Dev. 10:2527–2539). The phosphorylation site recognized by GSK-3 has been determined in several of these proteins (Plyte et al., 1992, supra). The diversity of these proteins belies a wide role for GSK-3 in the control of cellular metabolism, growth, and development. GSK-3 tends to phosphorylate serine and threonine residues in a proline-rich environment, but does not display the absolute dependence upon these amino acids which is displayed by protein kinases which are members of the mitogen-activated protein (MAP) kinase or cdc2 families of kinase enzymes.

Among the proteins which are phosphorylated by GSK-3 is c-Jun, the expression product of the c-jun proto-oncogene and the cellular homolog of the v-jun oncogene of avian sarcoma virus (Dent et al., 1989, FEBS Lett. 248:67–72). Jun acts as a component of the activator protein-1 (AP-1) transcription factor complex, which binds to a palindromic consensus binding site (the AP-1 site). c-Jun is both necessary and sufficient to induce transcription of genes having an AP-1 site (Angel et al., 1988, Nature 332:166–171; Angel et al., 1988, Cell: 55:875–885; Chiu et al., 1988, Cell 54:541–552; Bohmann et al., 1989, Cell 59:709–717; Abate et al., 1990, Mol. Cell. Biol. 10:5532–5535). Transcription of a gene having an AP-1 site may be initiated by either a Fos-Jun heterodimer or by a Jun-Jun homodimer, although the Fos-Jun heterodimer binds to DNA more stably than the Jun-Jun homodimer and is consequently a more potent transcription activator. Fos is the expression product of another proto-oncogene, c-fos (Schonthal et al., 1988, Cell 54:325–334; Sassone-Corsi, 1988, Nature 334:314–319). Phosphorylation of c-Jun by GSK-3 severely reduces the binding affinity of Jun-Jun homodimer for AP-1 sites (Boyle et al., 1991, Cell 64:573–584; Plyte et al., 1992, supra).

GSK-3 is a negative regulator of the wnt signaling pathway. The wnt pathway is a highly conserved signaling pathway that regulates cell fate decisions in both vertebrates and invertebrates (Perrimon, 1994, Cell 76:781–784; Perrimon, 1996, Cell 86:513–516; Miller et al., 1996, Genes & Dev. 10:2527–2539). Much of the pathway has been determined from detailed genetic analysis in Drosophila. At present, identified components of this signaling pathway include wnts (the secreted ligand), frizzled (the wnt receptor), and the intracellular mediators disheveled, GSK-3 (denoted zw3/sgg in Drosophila), and β-catenin (denoted armadillo in Drosophila). In 10T1/2 cells, wnt signaling inhibits GSK-3 p enzymatic activity (Cook et al., 1996, EMBO J. 15:4526–4536). This result is consistent with epistasis experiments in Drosophila which suggest an inhibitory role for GSK-3β/zw3/sgg in the wnt pathway. Wnt signaling leads to stabilization of β-catenin protein in Drosophila (Peifer et al., 1994, Dev., 120:369–380; van Leeuwen, et al., 1994, Nature 368:342–344) as well as Xenopus (Yost et al., 1996, Genes & Dev., 10:1443–1454). It has also been demonstrated that treatment of Drosophila S2 cells with LiCl leads to accumulation of armadillo protein (Stambolic et al., 1996, Curr. Biol. 6:1664–1668). Stabilization of β-catenin is associated with translocation of β-catenin to the nuclei of cells responding to wnt signaling (Funayama et al., 1995, J. Cell Biol., 128:959–968; Schneider et al., 1996, Mech. Dev., 57:191–198; Yost et al., 1996, supra). In addition, ectopic expression of conserved genes, including wnts, disheveled, and β-catenin, leads to second axis formation in Xenopus. Second axis formation in Xenopus is also observed following lithium treatment. Although β-catenin was originally discovered as a cadherin-binding protein, it has recently been shown to function as a transcriptional activator when complexed with members of the Tcf family of DNA binding proteins (Molenaar et al., 1996, Cell 86:391; Behrens et al., 1996, Nature 382:638).

There exists a pressing need to identify compositions which have the therapeutic effect of lithium without the attendant side effects which accompany administration of lithium to human patients.

SUMMARY OF THE INVENTION

The invention relates to a method of identifying a GSK-3 inhibitor comprising providing a mixture comprising GSK-3, a source of phosphate, a GSK-3 substrate and a GSK-3 assay buffer, incubating the mixture in the presence or absence of a test compound, and measuring the level of phosphorylation of the GSK-3 substrate, wherein a lower level of phosphorylation of the GSK-3 substrate in the presence of the test compound compared with the level of phosphorylation of the GSK-3 substrate in the absence of the test compound is an indication that the test compound is a GSK-3 inhibitor.

The method of identifying a GSK-3 inhibitor may be performed either in vitro wherein the assay mixture is cell-free, in vitro wherein live cells are included in the assay, or in vivo in an animal.

The GSK-3 may be provided in the assay mixture as a protein or as a nucleic acid, either DNA or RNA, from which GSK-3 is expressed.

In one aspect of the invention, the mixture is contained within a eukaryotic cell.

In one embodiment of the invention, at least one of the GSK-3, the GSK-3 substrate and the test compound is injected into the eukaryotic cell prior to the incubation. In another embodiment, at least two of the GSK-3, the GSK-3 substrate and the test compound are injected into the eukaryotic cell prior to the incubation. In yet another embodiment, the GSK-3, the GSK-3 substrate and the test compound are injected into the eukaryotic cell prior to the incubation.

In another embodiment of the invention, the eukaryotic cell is suspended in a solution comprising the test compound.

The eukaryotic cell is selected from the group consisting of a *Xenopus laevis* oocyte, a *Xenopus laevis* embryo cell, a mammalian cell, a *Drosophila melanogaster* S2 cell, a *Dictyostelium discoideum* cell and a yeast cell. Preferably, the eukaryotic cell is selected from the group consisting of a *Xenopus laevis* oocyte and a *Xenopus laevis* embryo cell. More preferably, the eukaryotic cell is a *Xenopus laevis* oocyte which even more preferably, is a *Xenopus laevis* embryo cell, yet more preferably, a *Xenopus laevis* embryo ventral vegetal blastomere cell.

In one aspect of the invention, the phosphate source comprises a nucleotide triphosphate selected from the group consisting of ATP and GTP and preferably comprises a detectable label which is transferred to the substrate during the incubation. More preferably, the phosphate source comprises $[\gamma^{32}P]$-ATP.

The GSK-3 which is contained within the mixture may be endogenous in the eukaryotic cell.

Preferably, the GSK-3 is selected from the group consisting of human GSK-3α, human GSK-3β, *Xenopus laevis* GSK-3α, *Xenopus laevis* GSK-3β, bacterially-expressed *Xenopus laevis* GSK-3β, bacterially-expressed rat GSK-3β, the expression product of the *Drosophila melanogaster* zw3/sgg gene, and the expression product of the *Dictyostelium discoideum* gskA gene. More preferably, the GSK-3 is bacterially-expressed rat GSK-3β.

The GSK-3 substrate which is contained within the mixture may also be endogenous in the eukaryotic cell.

Preferably, the GSK-3 substrate is selected from the group consisting of glycogen synthase, phosphatase inhibitor I-2, cAMP-dependent protein kinase type II subunit, phosphatase-1 G-subunit, ATP-citrate lyase, acetyl coenzyme A carboxylase, myelin basic protein, a microtubule-associated protein, a neurofilament protein, an N-CAM cell adhesion molecule, nerve growth factor receptor, c-Jun, JunD, c-Myb, c-Myc, L-myc, adenomatous polyposis coli tumor suppressor protein, τ protein, β-catenin, peptide GS-2, and peptide derivatives of any of these which comprise a GSK-3 phosphorylation site. More preferably, the GSK-3 substrate comprises τ protein.

The test compound used in the method of the invention is selected from the group consisting of bis-indolyl maleimides, staurosporine and derivatives thereof, and protein kinase C inhibitors.

The invention also includes a GSK-3 inhibitor which is identified by a method comprising providing a mixture comprising GSK-3, a source of phosphate, a GSK-3 substrate and a GSK-3 assay buffer, incubating the mixture in the presence or absence of a test compound, and measuring the level of phosphorylation of the GSK-3 substrate, wherein a lower level of phosphorylation of the GSK-3 substrate in the presence of the test compound compared with the level of phosphorylation of the GSK-3 substrate in the absence of the test compound is an indication that the test compound is a GSK-3 inhibitor.

Also included in the invention is a method of treating a GSK-3-related disorder in an animal comprising administering to the animal a GSK-3 inhibitor suspended in a pharmaceutically acceptable carrier. Preferably, the animal is a mammal, and more preferably, the mammal is a human.

The GSK-3 related disorder which is treated according to the method of the invention is preferably selected from the group consisting of bipolar disorder including mania, Alzheimer's disease, diabetes, and leukopenia.

Lithium is recognized as a potent stimulator of hematopoiesis, both in vivo and in vitro (Doukas et al., 1986, Exp. Hematol. 14:215–221). Treatment of cyclic hematopoiesis in the grey collie dog with lithium carbonate eliminated the recurrent neutropenia and normalized the other blood cell counts (Hammond et al., 1980, Blood 55:26–28). Furthermore, lithium has been observed to stimulate in vitro Dexter culture hemopoiesis, leading to increases in granulocyte, megakaryocytes, and pluripotent stem cell numbers. In one study in a murine Dexter culture system, exposure of Dexter cultures to 1 mM LiCl prior to culture resulted in greater hemopoiesis than was observed in Dexter cultures which were not exposed to LiCl (Quesenberry et al., 1984, Blood 63:121–127). These findings suggest that human cyclic hematopoiesis, including leukopenia, may be successfully treated with lithium.

The GSK-3 inhibitor which is used to treat a GSK-3 related disorder is preferably Ro31-8220 or structurally-related compounds.

The invention also relates to a method of reducing motility of mammalian spermatozoa comprising administering to the spermatozoa a GSK-3 inhibitor suspended in a pharmaceutically-acceptable carrier. Lithium has been demonstrated to inhibit the motility of swimming spermatozoa.

BRIEF DESCRIPTION OF THE DRAWINGS

FIG. 6 is a series of images of Western blots which depict in vivo inhibition of GSK-3β by lithium. Panel A is a pair of images which depict in vivo inhibition of GSK-3β by lithium in Xenopus laevis oocytes. Oocyte culture and injection methods are described in Example 1. Oocytes were injected with mRNA specifying Xenopus laevis GSK-3β (lanes 1, 3, and. 4) or with mRNA specifying Dictyostelium discoideum GSK-3β (lanes 5 and 6), and were then incubated overnight at 18° C. Following incubation, oocytes were transferred to OR2+medium which contained either 0 mM LiCl (lanes 1, 2, 3, and 5) or 20 mM LiCl (lanes 4 and 6), and were then injected with τ protein (except lane 2). Following 2 hours in cubation in the respective media, oocytes were harvested and lysed, and the lysate was subjected to SDS-polyacrylamide gel electrophoresis. Western blot analysis was performed using antibody PHF-1 or using antibodies T14/T46 described herein.

Panel B is an image of a Western blot which depicts the presence of GSK-3β protein in Xenopus oocytes which were injected with mRNA specifying Dictyostelium discoideum GSK-3β (lanes 2 and 3) and which were incubated in medium which contained either no LiCl (lanes 1 and 2) or 20 mM LiCl (lane 3). Following 2 hours incubation in the respective media, oocytes were harvested and lysed, and the lysate was subjected to SDS-polyacrylamide gel electrophoresis. Western blot analysis was performed using an antibody which recognizes GSK-3.

Panel C is a pair of images of Western blots which depict the results from a dose-response experiment to test lithium inhibition of GSK-3β. Xenopus oocytes were injected with mRNA specifying Xenopus GSK-3β as in Panel A. Following overnight incubation, the oocytes were transferred to OR2+medium which contained the indicated concentrations of LiCl, and were then injected with τ protein. Following 2 hours incubation in the respective media, oocytes were harvested and lysed, and the lysate was subjected to SDS-polyacrylamide gel electrophoresis. Western blot analysis was performed using antibody PHF-1 or using T14/T46 antibodies.

Figure 7A:
Figure 7B:
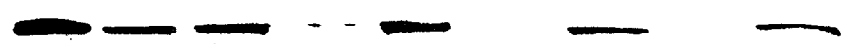
Figure 7C:
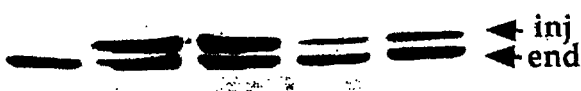

FIG. 7 is a series of images which depict Western blot analyses which were performed using an antibody which recognizes B-catenin. In Panel A, Xenopus oocytes were injected with mRNA specifying β-catenin. The oocytes were also injected with mRNA specifying DN-GSK-3 (lane 3) or with mRNA specifying wildtype GSK-3 mRNA (lane 4). The oocytes were incubated overnight in OR2+medium. The oocytes corresponding to lane 2 were incubated in medium further comprising 20 mM LiCl. Following incubation in the respective media, oocytes were harvested and lysed, and the lysate was subjected to SDS-polyacrylamide gel electrophoresis and Western blot analysis. In Panel B, stage 6 Xenopus oocytes were injected with β-catenin protein. The oocytes were incubated in OR2+medium which contained no LiCl, or in OR2+medium which contained 20 mM LiCl, for 0, 1, 2, 4, or 6 hours. Following incubation in the respective media, oocytes were harvested and lysed, and the lysate was subjected to SDS-polyacrylamide gel electrophoresis and Western blot analysis. Lane titles include a digit which identifies the number of hours of incubation and further include a "+" or "−" designation, denoting oocytes which were incubated in the presence (+) of LiCl, and oocytes which were incubated in the absence (−) of LiCl. The lane entitled "un" is the lane to which protein from cells not injected with β-catenin protein was applied. In Panel C, two-cell Xenopus embryos were injected with β-catenin protein. As described in Example 2, some embryos were treated with LiCl. Embryos were harvested immediately after lithium treatment or following 4 hours of incubation, when the embryos had reached the blastula stage. In the lanes entitled "0" and "4", these numbers indicate the number of hours the embryos corresponding to that lane were incubated, and "+" indicates that the embryos corresponding to that lane were treated with LiCl. "Un" indicates that the embryos corresponding to that lane were not injected with β-catenin protein. Exogenous β-catenin, which is labeled "inj," can be distinguished from endogenous β-catenin, which is labeled, "end."

Figure 8A:
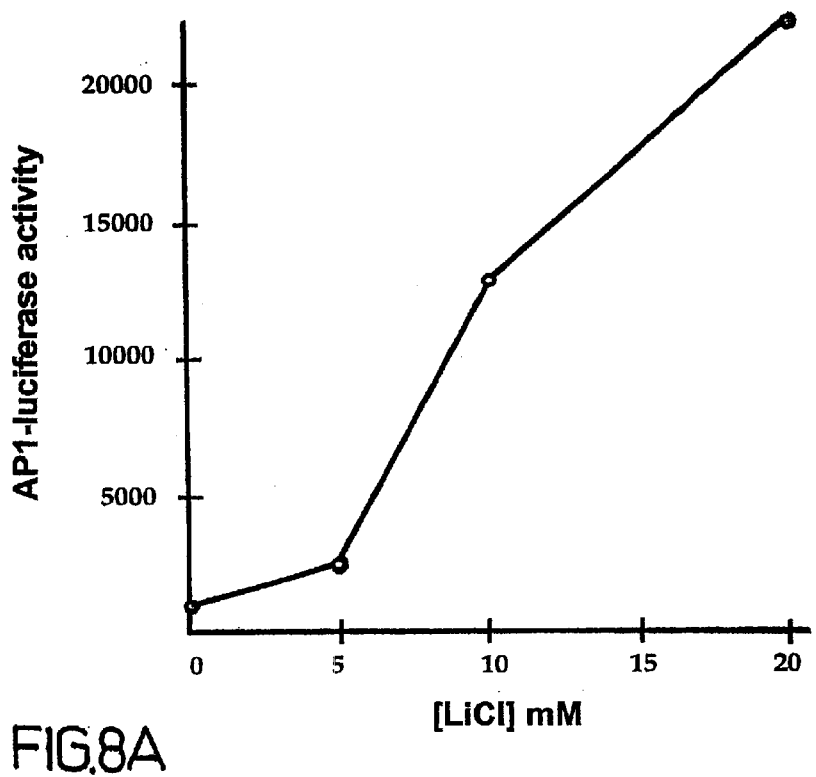
Figure 8B:
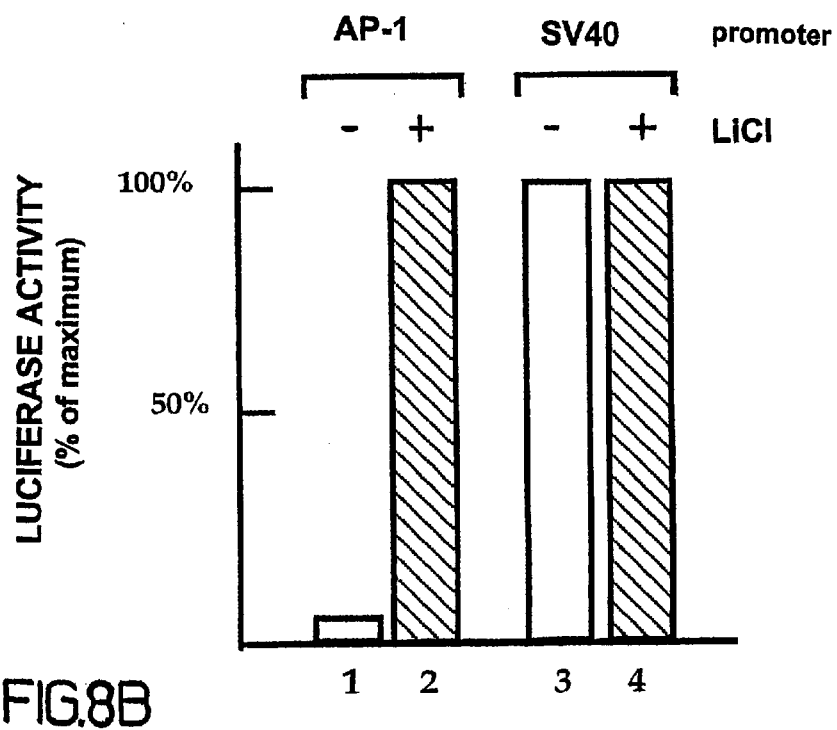

FIG. 8 is a pair of graphs depicting the results of experiments which were conducted to confirm the ability of LiCl to induce transcription of genes having an AP-1 site. In Panel A, 1-cell embryos were injected with a reporter plasmid, AP1-luc, and were cultured in medium containing 0, 5, 10, or 20 mM LiCl. Plasmid AP1-luc comprises an AP-1 site, a minimal promoter, and the luciferase gene. Embryos were harvested at stage 12, and were assayed for luciferase activity as described in Example 2. The graph in Panel A depicts luciferase activity in embryo lysate as a function of LiCl concentration in the incubation medium. Panel B is a graph which compares luciferase activity in lysate from embryos injected with AP1-luc with luciferase activity in lysate from embryos injected with a control plasmid, SV40-luc. SV40-luc comprises the coding sequence of luciferase fused to the SV40 promoter sequence. Xenopus embryos were injected at the one-cell stage with plasmid AP1-luc or with plasmid SV40-luc and were incubated in 0.1×MMR medium containing 0 or 20 mM LiCl. When the embryos reached stage 12, they were harvested and lysed, and luciferase activity in the lysate was assessed.

Figure 9A:
Figure 9B:

FIG. 9 is a pair of images which depict *Xenopus laevis* embryos. Embryos were injected into a ventral-vegetal blastomere at the 16-cell stage with mRNA specifying DN-GSK-3 and with either water or myo-inositol. Panel A depicts an embryo which was injected with mRNA specifying DN-GSK-3 and water. Panel B depicts an embryo which was injected with mRNA specifying DN-GSK-3 and myo-inositol.

DETAILED DESCRIPTION OF THE INVENTION

The invention is based on the discovery that lithium inhibits the activity of GSK-3 both in vitro and in vivo in an animal. In view of this discovery, the present invention includes methods of identifying lithium substitute compounds which have the therapeutic effect of lithium without the attendant side effects of lithium. Further in view of the discovery of inhibition of GSK-3 by lithium, the invention also includes methods of treating a GSK-3 related disorder in an animal, preferably a human, by administering to the animal an inhibitor of GSK-3.

The present invention thus includes the identification of compounds and methods of use thereof which inhibit GSK-3 and which are therefore of therapeutic benefit to an animal, preferably a human, having a GSK-3-related disorder.

Because GSK-3 is broadly conserved across the phylogenetic spectrum and because GSK-3 has been implicated in numerous metabolic and regulatory processes in cells, compounds which modulate the activity of GSK-3 in vivo are useful for the treatment of a variety of diseases and conditions including, but not limited to, bipolar disorder (particularly mania), diabetes, Alzheimer's disease, and leukopenia. Compounds which modulate GSK-3 activity are also useful as contraceptive compounds. The discovery that the action of lithium is mediated by inhibition of GSK-3 renders the assays of the invention useful for the identification of compounds which have lithium-like activity.

The assays of the invention are useful for identifying compounds which inhibit GSK-3 activity. Essentially any metabolic or other disorder or condition which relies on the activity of GSK-3 for the expression of that disorder or condition is a potential therapeutic target for compounds which inhibit GSK-3 in the assays of the invention. For example, sperm motility is known to be inhibited by lithium. Thus, in addition to the aforementioned disorders and conditions, compounds which inhibit GSK-3β activity in the assays of the invention may even be useful as male contraceptives.

As used herein, the term "GSK-3" means the enzyme glycogen synthase kinase 3 and its homologs. As discussed herein, GSK-3 is conserved among organisms across the phylogenetic spectrum, although the homologs present in various organisms differ in ways that are not significant for the purposes of the present invention. One of skill in the art will appreciate that the present invention may be practiced using any of the eukaryotic homologs of GSK-3 (e.g. see FIG. 6, Panel B). Furthermore, vertebrate GSK-3 exists in two isoforms, denoted GSK-3α and GSK-3β. GSK-3α and GSK-3β differ from one another only in ways that are not significant for the purposes of the present invention. Therefore, the terms "GSK-3", "GSK-3α", and "GSK-3β" are used interchangeably herein. Although the Examples presented herein exemplify the study and use of GSK-3β, the invention should not be considered to be limited to this particular isoform of GSK-3.

The invention relates to a method of identifying a GSK-3 inhibitor comprising providing a mixture comprising GSK-3, a source of phosphate, a GSK-3 substrate and a GSK-3 assay buffer, incubating the mixture in the presence or absence of a test compound, and measuring the level of phosphorylation of the GSK-3 substrate. A lower level of phosphorylation of the GSK-3 substrate in the presence of the test compound compared with the level of phosphorylation of the GSK-3 substrate in the absence of the test compound is an indication that the test compound is a GSK-3 inhibitor.

In the assay of the invention, GSK-3 may be provided as a protein or it may be provided in the assay mixture as an mRNA specifying GSK-3. When the assay comprises cell-free components, GSK-3 is provided as the protein. When the assay is conducted in the milieu of a cell, GSK-3 may be provided as either the protein or as an mRNA specifying GSK-3, wherein, in order that GSK-3 be available in the assay, the mRNA is translated and GSK-3 protein is thereby produced. It will be apparent from the Examples provided herein that it is a simple matter to obtain mRNA specifying GSK-3 and inject the mRNA into a cell for production of GSK-3 protein. GSK-3 may also be provided by expression of a plasmid which encodes GSK-3. Standard molecular biology techniques may be used to construct operable plasmids encoding GSK-3 and to express the plasmid in cells (Sambrook, et al., 1989, In: Molecular Cloning: A Laboratory Manual, Cold Spring Harbor Laboratory, New York).

As discussed herein, the method of identifying a GSK-3 inhibitor may be performed either in vitro wherein the assay mixture is cell-free, in vitro wherein live cells are included in the assay, or in vivo in an animal. Thus, in one aspect of the invention, the mixture is contained within a eukaryotic cell and the method of the invention may be performed wherein some of the components of the assay mixture may be provided exogenously to a cell my microinjection of the components therein, and some of the components may be endogenous in the cell.

The term "endogenous in the cell" as used herein, means that the component is naturally produced in the subject cell.

The term "exogenous to the cell" as used herein, means that the component is not found naturally in the subject cell, or is found therein at a low level, and is added thereto.

When the method of the invention is performed using a eukaryotic cell, one or more of the GSK-3, the GSK-3 substrate and the test compound may be injected into the eukaryotic cell prior to the incubation. The cell so injected is then incubated under conditions which facilitate GSK-3 activity and the level of GSK-3 activity is subsequently measured following the incubation period using the assays described herein.

The eukaryotic cell which is useful in the methods of the invention may be any one of a *Xenopus laevis* oocyte, a *Xenopus laevis* embryo cell, a mammalian cell (such as a 10T1/2 cell), a *Drosophila melanogaster* S2 cell, a *Dictyostelium discoideum* cell and a yeast cell. Preferably, the eukaryotic cell is either a *Xenopus laevis* oocyte or a *Xenopus laevis* embryo cell. More preferably, the eukaryotic cell is a *Xenopus laevis* oocyte, and even more preferably, the eukaryotic cell is a *Xenopus laevis* embryo cell. Still more preferably, the eukaryotic cell is a *Xenopus laevis* embryo ventral vegetal blastomere cell. Methods of obtaining the described cell for use in the present invention are well known in the art and are described, for example, in the Examples provided herein.

The source of phosphate for use in the methods of the invention may be any common source of phosphate, including, but not limited to, a nucleotide triphosphates such as, but not limited to, ATP or GTP. In a preferred embodiment, the phosphate source has bound thereon a detectable label which label is transferred with the phosphate group to the GSK-3 substrate during the reaction. In this manner, phosphorylated GSK-3 substrate may be distinguished from non-phosphorylated GSK-3 substrate in that the phosphorylated substrate will contain the detectable label whereas the non-phosphorylated substrate will not contain the label. In another embodiment, the phosphate source does not have bound thereon a detectable label; instead, phosphorylated GSK-3 substrate may be distinguished from non-phosphorylated GSK-3 substrate, for instance by recognition of one form of the substrate, but not the other, by an antibody. As described in the Examples provided herein, the extent of phosphorylation of a GSK-3 substrate following incubation with GSK-3 under the described conditions, is a direct measure of GSK-3 activity. Thus, any reduction in the level of phosphorylation of a GSK-3 substrate in the presence of a putative GSK-3 inhibitor is an indication that the putative inhibitor is a GSK-3 inhibitor.

The detectable label which is useful in the methods of the invention may include any known or heretofore unknown detectable label which is transferred to the GSK substrate upon transfer of a phosphate group thereto as a result of GSK-3 activity. Labels which are useful include, but are not limited to, radioactive labels, such as $\gamma^{32}P$, $^{35}S$, and non-radioactive labels, such as biotin and the like.

The GSK-3 which is useful in the invention is any eukaryotic GSK-3. The GSK-3 which is useful includes, but is not limited to, human GSK-3α, human GSK-3β, *Xenopus laevis* GSK-3α, *Xenopus laevis* GSK-3β, bacterially-expressed *Xenopus laevis* GSK-3β, the expression product of the *Drosophila melanogaster* zw3/sgg gene, and the expression product of the *Dictyostelium discoideum* gskA gene. Preferably, the GSK-3 is bacterially-expressed *Xenopus laevis* GSK-3β.

By the term "bacterially-expressed" as used herein, is meant a protein which has been produced in bacteria, which bacteria are transformed with DNA encoding the protein using recombinant DNA technology.

There are many GSK-3 substrates which are useful in the methods of the invention. GSK-3 substrates which are useful include, but are not limited to, glycogen synthase, phosphatase inhibitor I-2, cAMP-dependent protein kinase type II subunit, phosphatase-1 G-subunit, ATP-citrate lyase, acetyl coenzyme A carboxylase, myelin basic protein, a microtubule-associated protein, a neurofilament protein, an N-CAM cell adhesion molecule, nerve growth factor receptor, c-Jun, JunD, c-Myb, c-Myc, L-myc, adenomatous polyposis coli tumor suppressor protein, τprotein, β-catenin, peptide GS-2, and peptide derivatives of any of these which comprise a GSK-3 phosphorylation site. Preferably, the GSK-3 substrate which is useful in the methods of the invention is τ protein. GS-2 peptide is another GSK-3 substrate which is preferred in the methods of the invention. Many of the aforementioned substrates are available in the art, either in the scientific literature or from commercial sources. Methods of obtaining several of these substrates are described herein in the Experimental Details section.

The test compound used in the method of the invention may include bis-indolyl maleimides and structurally related compounds, staurosporine, derivatives thereof, and structurally-related compounds of a class known to inhibit other protein kinases, particularly those compounds known to inhibit protein kinase C.

The identification of an inhibitor which inhibits the activity of GSK-3 provides useful methods for treatment of GSK-3 related disorders in an animal, which methods are also included in the invention.

As used herein, the term "GSK-3 related disorder" means a metabolic or other disorder or condition which relies on the activity of GSK-3 for the expression of that disorder or condition. The term "GSK-3 related disorder" includes all disorders and conditions which are known to be treatable with lithium.

Essentially, a method is provided wherein a GSK-3 related disorder in an animal is treated by administering to the animal an inhibitor of GSK-3 suspended in a pharmaceutically acceptable carrier. Preferably, the animal is a mammal, and more preferably, the mammal is a human.

The route of administration of a GSK-3 inhibitor to an animal will depend upon a number of factors including the type of inhibitor used, the disorder being treated, the age of the animals and the severity of the disorder. The inhibitor is prepared for administration to the animal by being suspended or dissolved in a pharmaceutically acceptable carrier such as isotonic saline, isotonic salts solution or other formulations which will be apparent to those skilled in such administration.

The inhibitor may be administered to an animal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema). Preferably, for treatment of patients having lung infection, the route of administration is intranasal delivery by aerosol or via the blood. The appropriate pharmaceutically acceptable carrier will be evident to those skilled in the art and will depend in large part upon the route of administration.

Treatment regimes which are contemplated include a single dose of inhibitor or dosage which is administered hourly, daily, weekly or monthly, or yearly. Dosages may vary from 1 μg to 1000 mg/kg of body weight of the GSK-3 inhibitor, and will be in a form suitable for delivery of the compound to the animal.

The GSK-3 related disorder which is treated according to the method of the invention is preferably selected from the group consisting of bipolar disorder including mania, Alzheimer's disease, diabetes, and leukopenia.

The GSK-3 inhibitor which is used to treat a GSK-3 related disorder is preferably Ro31-8220.

The invention also relates to a method of reducing motility of mammalian spermatozoa comprising administering to the spermatozoa a GSK-3 inhibitor suspended in a pharmaceutically-acceptable carrier. Preferably, the GSK-3 inhibitor used in this method of the invention is Ro31-8220.

The assays of the invention are useful for screening test compounds for the ability to inhibit GSK-3 activity. To screen test compounds, any of the GSK-3 assays described herein may be used. Preferably, test compounds are first screened using the in vitro assays described herein, and those test compounds which exhibit the ability to inhibit the activity of GSK-3 are then screened using the in vivo assays described herein.

To screen a test compound using either the in vitro or the in vivo assays described herein, at least a pair of assay mixtures is provided. The test compound to be screened is added to one assay mixture in each pair, and is not added to the other assay mixture in the pair. GSK-3 activity is determined in each assay mixture of the pair. If the test compound is a GSK-3 inhibitor, then GSK-3 activity will be lower in the assay mixture which contains the test compound than in the assay mixture which does not contain the test compound. One skilled in the art will appreciate that it is desirable to screen test compounds using several different concentrations of the test compound in different assay pairs.

To screen a test compound in vivo in an animal, an animal having cells which express GSK-3 is selected. The test compound is administered to at least one animal, and at least one other animal is not administered the test compound. The activity of GSK-3 in each animal may be assessed in numerous ways, including observation of a macroscopic trait which is influenced by the level of GSK-3 activity in the animal, analysis of the composition of a tissue sample, such as a blood sample, which composition is influenced by the level of GSK-3 activity in the animal, measurement of GSK-3 activity in a tissue sample of the animal, and others methods known to those of skill in the art.

The invention is now described with reference to the Examples contained within Experimental Details section presented herein. It should be appreciated that the invention should not be construed to be limited to the Examples which are now described. Rather, the invention should be construed to include any and all applications provided herein and all equivalent variations which are within the skill of the skilled artisan.

Example 1

Inhibition of GSK-3β by Lithium in vitro

The materials and methods used in Example 1 are now described.

Sources of Chemicals and Proteins

Purified, bacterially-expressed GSK-3β, casein kinase II, and phosphatase inhibitor-2 (I-2) were purchased from New England Biolabs (Beverly, Mass.). Glutathione-S-transferase-extracellular signal-related kinase 1 (GST-ERK-1, also known as MAP kinase) is known in the art and is available to the public (e.g. from UBI, Upstate Biotechnology Incorporated, Lake Placid, N.Y.). For the experiments described in Example 1, GST-ERK-1 was provided by Sandro Allesandrini and Ray Erickson (Harvard University). Protein kinase A was obtained from Sigma (St. Louis, Mo.). L-690,330 was obtained from Tocris Cookson (St. Louis, Mo.; see Atack et al., 1993, J. Neurochem. 60:652–658 and Atack et al., 1994, J. Pharmacol. Exp. Ther. 270:70–76). Tritium labeled inositol-1-phosphate (1.0 Ci/mmol, 25 μCi/ml) was obtained from American Radiolabeled Chemicals (St. Louis, Mo.). [$\gamma^{32}$P]-ATP (3000 Ci/mmol) was obtained from Amersham (Arlington Heights, Ill.). Bacterially-expressed τ protein was synthesized according to a described method (Goedert et al., 1990, EMBO J. 9:4225–4230). τ protein purified from bovine brain tissue is commercially available (e.g. from Sigma Chemical Company, St. Louis, Mo.).

Embryos and Microinjection

Xenopus eggs were fertilized in vitro according to well established protocols (Peng, 1991, in Appendix A of Methods in Cell Biology, Kay et al., eds., Academic Press Inc, San Diego). Microinjection of embryos was performed using embryos at the 1-cell to 32-cell stage, and a volume of 5–10 nl was injected into each embryo. Following microinjection, embryos to be treated with lithium were incubated for 6 minutes in 0.1×Modified Marc's Ringer's solution (MMR; 0.1 M NaCl, 2.0 mM KCl, 1.0 mM $MgCl_2$, 2.0 mM $CaCl_2$, 0.1 mM EDTA, 5.0 mM HEPES, pH 7.4; Peng, 1991, supra) containing 0.3 M LiCl, and the lithium-treated embryos were then washed in 0.1×MMR as described (Kao et al., 1986, Nature 322:371–373).

Alternatively, 5 nl of 0.3 M LiCl was microinjected into a ventral vegetal blastomere of an embryo at the 16- or 32-cell stage (Busa et al., 1989, Dev. Biol. 132:315–324).

L-690,330 was dissolved in water to form a solution having a concentration of L-690,330 in the range of 0.1 to 10 mM, and 5 to 10 nl of the L-690,330 solution was injected into the ventral vegetal region of 4, 8, 16, and 32 cell embryos. All four cells of individual 4-cell embryos were injected in separate experiments.

IMPase Activity

Thirty Xenopus embryos at the 32-cell stage were washed with 1 ml of 50 mM Tris, pH 7.8, 250 mM KCl, 3 mM $MgCl_2$ (IMPB). The thirty embryos were then lysed in 300 μl of IMPB. The lysate was centrifuged for 5 minutes at 20,000×g at 4° C. and the resulting lysate supernatant was recovered. The lysate supernatant was divided into 25 μl aliquots, to each of which was added 2.5 μl of water, 2.5 μl of a LiCl solution, or 2.5 μl of an L-690,330 solution. Each lysate supernatant mixture was then incubated at room temperature for 5 minutes. One μl of $^3$H-inositol-1-phosphate was added to each lysate supernatant mixture, and the incubation was continued for an additional 25 minutes. Each lysate supernatant mixture was then diluted with 1.0 ml of 0.1×MMR, boiled for 5 minutes, and applied to Dowex columns as described (Berridge et al., 1983, Biochem. J.

212:473–482). Inositol was not retained by the Dowex column, and inositol-1-phosphate was eluted by application of 3 ml of 0.1 M formic acid/1.5 M ammonium formate (Berridge et al., 1983, supra). Each assay was repeated two to four times, and similar results were obtained among all replicates.

To assay IMPase activity in vivo, an $^3$H-inositol-1-phosphate solution having a concentration of 250 $\mu$Ci/ml was mixed with an equal volume of a solution which comprised water, 10 mM L-690,330, or 0.6 M LiCl. Following dilution, 10 nl of the diluted $^3$H-inositol-1-phosphate solution was injected into a single ventral-vegetal blastomere of an embryo which was at the 8- to 16-cell stage. After ten minutes, twenty embryos were lysed in 1.0 ml of a boiling solution which comprised 0.1×MMR and 20 mM LiCl. The lysate was prepared and applied to Dowex columns as described above.

GSK-3β Activity

GSK-3β was assayed as described in the following paragraph using 0.5–1.0 units of GSK-3β per assay. One unit of GSK-3β activity is defined as the amount of GSK-3β required to catalyze the transfer of 1 pmol of phosphate to protein substrate I-2 in 1 minute at 30° C. in GSK-3 buffer in a 25 $\mu$l reaction volume (Wang et al., 1994, Biochem. 33:143–147). GSK-3 buffer comprises 20 mM Tris-HCl, 10 mM MgCl$_2$, 5 mM dithiothreitol, and has a pH of 7.5 at 20° C. GSK-3β supplied by New England Biolabs is isolated from a strain of Escherichia coli that contains a clone of GSK-3β which was derived from a rabbit skeletal muscle cDNA library (Wang, et al., 1994, J. Biol. Chem. 269:14566–14574).

The assay mixture comprised 1×GSK-3 buffer, an amount of a kinase enzyme corresponding to 0.5–1.0 unit of activity, a substrate, and 200 $\mu$M [$\gamma^{32}$P]-ATP (approximately 500 $\mu$Ci/$\mu$mol). The assay mixture was incubated for a selected period of time following which incorporation of $^{32}$P into the substrate was determined by standard methods.

When the peptide, GS-2, was used as the substrate for GSK-3β in the assay, GS-2 was present at 25 $\mu$M and incorporation of $^{32}$P into GS-2 was measured by binding GS-2 to P81 paper according to previously described methods (Stokoe et al., 1992, EMBO J. 11:3985–3994). GS-2 was synthesized with phosphate incorporated into the serine closest to the carboxyl terminus and has the sequence RPASYPPSPSLSRHSSPHQS(P)EDEEE (SEQ ID No:1) (Fiol et al., 1987, J. Biol. Chem. 262:14042–14048). When I-2 was used as the substrate for GSK-3 P in the assay, I-2 was present at a concentration of 50 $\mu$g/ml. When bacterially-expressed τ protein (Goedert et al., 1990, EMBO J. 9:4225–4230) was used as the substrate for GSK-3β in the assay, τ protein was present at a concentration of 25 $\mu$g/mL. The activities of protein kinase A (PKA), mitogen-activating protein kinase (ERK-1/MAP kinase), and casein kinase II (CKII) were assayed under conditions similar to those used to assay GSK-3$\mu$ activity, except that β-mercaptoethanol was included in the PKA assays.

In PKA assays, kemptide was used as the substrate for PKA at a concentration of 50 $\mu$M. In ERK-1/MAP kinase assays, myelin basic protein (MBP) was used as the substrate for ERK-1/MAP kinase at a concentration of 0.5 $\mu$g/$\mu$l. In CKII assays, casein was used as the substrate for CKII at a concentration of 50 $\mu$g/ml. GSK-3β phosphorylation of I-2, but not of GS-2 or of τ protein, was partially inhibited by 20 mM KCl or 20 mM NaCl.

The results obtained in the experiments presented in Example 1 are now described.

The Role of Inositol Monophosphatase in Xenopus Development

Figure 1A:
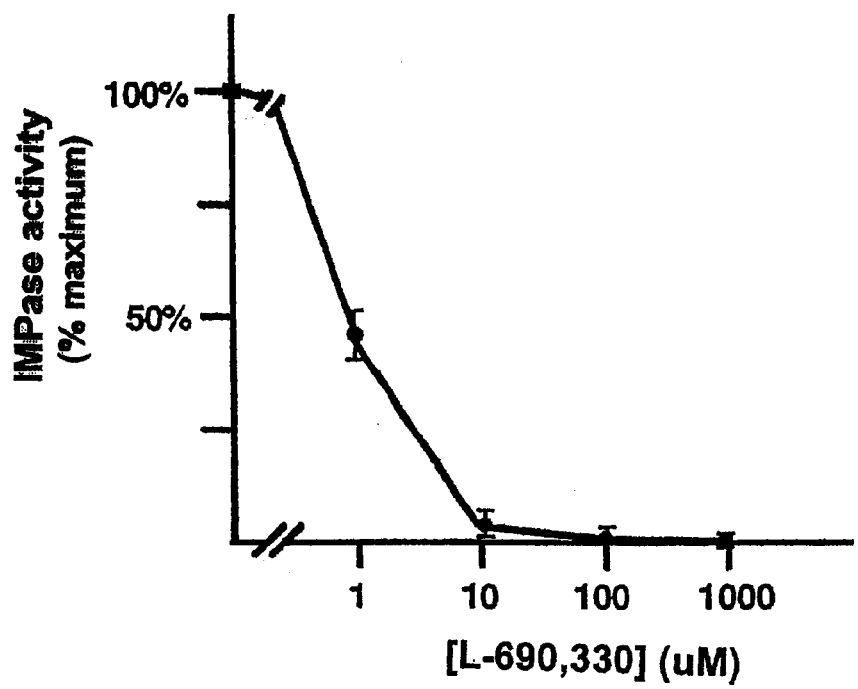
FIG. 1 comprises Panels A, B and C. Panel A is a graph which depicts IMPase activity as a function of the concentration of L-690,330 in the assay mixture. L-690,330 is an inhibitor of IMPase activity. IMPase activity was measured as described in Example 1. Approximately 50% inhibition of IMPase activity was observed when the concentration of L-690,330 in the assay mixture was 1 mM. Panel B is a graph which depicts in vivo IMPase activity measured in ventral-vegetal blastomeres which were injected with 10 nl of water, with 10 nl of a solution containing 0.3 M LiCl, or with 10 nl of a solution containing 5 mM L-690,330. Panel C is a trio of images, each of which depicts a stage 30 *Xenopus laevis* embryo which had been injected with one of three solutions. The embryo depicted in the image labeled, 'Control,' was injected at the 16-cell stage with 10 nl of water. The embryo depicted in the image labeled, 'LiCl,' was injected at the 16-cell stage with 10 nl of a solution containing 0.3 M LiCl. The embryo depicted in the image labeled 'L-690,330,' was injected at the 16-cell stage with a solution containing 5 mM L-690,330.
Figure 1B:
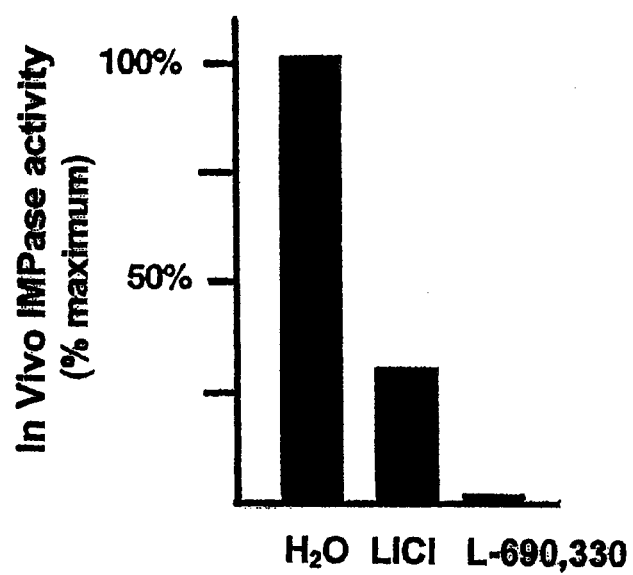

In order to determine the role of inositol monophosphatase (IMPase) in Xenopus development, the activity of IMPase was assessed in the presence of a competitive inhibitor of IMPase, L-690,330. The bisphosphonate compound L-690,330, is an approximately thousand-fold more potent inhibitor of IMPase activity than is lithium (Atack et al., 1993, J. Neurochem. 60:652–658). As indicated by the results depicted in FIG. 1, Panel A, L-690,330 effectively inhibited in vitro IMPase activity in lysates prepared from Xenopus embryos (50% inhibition at approximately 1 $\mu$M L-690,330). When microinjected into blastomeres at the 4, 8 to 16, and 32 cell stages, 10 nl of a solution containing 5 mM L-690,330 resulted in a level of inhibition of IMPase activity which was several times greater than the inhibition of IMPase activity which was observed when blastomeres were injected with 10 nl of a solution containing 0.3 M LiCl (FIG. 1, Panel B). When LiCl was microinjected into blastomeres at the 8 to 16 cell stage, IMPase activity was inhibited by roughly 75% relative to IMPase activity in the absence of LiCl (FIG. 1, Panel B).

Xenopus embryos were injected with 10 nl water, were incubated in 0.3M LiCl for 6 minutes at the 32-cell stage, or were injected with 10 nl of a solution comprising 5 mM L-690,330. The embryo which was incubated in the LiCl solution exhibited profound dorsalization, having a concentric cement gland, expanded anterior neural structures, and lacking ventral and posterior structures (FIG. 1, Panel C, image labeled 'LiCl'). The embryo which was injected with the solution containing L-690,330 did not exhibit dorsalization (FIG. 1, Panel C, image labeled 'L-690,330'). Similar results were obtained when ventral-vegetal blastomeres were injected at the 4, 8, or 32 cell stages. Similar results were also obtained when each cell of 4 cell stage embryos was injected. In no case was evidence of dorsalization observed following injection of an embryo with the solution containing L-690,330. Furthermore, L-690,330 had no discernible effect on development of Xenopus embryos microinjected therewith. At the highest doses of L-690,330 used in microinjected embryos, a mild nonspecific toxicity was observed. These results establish that inhibition of IMPase does not explain the dorsalizing effect of lithium on Xenopus development.

Because dorsalization caused by subjecting Xenopus embryos to lithium is phenotypically similar to ectopic expression of the wingless/int-1 related genes (wnt genes) in Xenopus embryos (McMahon et al., 1989, Cell 58:1075–1084), the experiments described herein were performed to determine whether lithium exerts its dorsalizing effects by interacting with a component of the wnt signaling pathway. The wnt pathway, which appears to be well conserved among both vertebrates and invertebrates (Pierce et al., 1995, Development 121:755–765; He et al., 1995, Nature 374:617–622; Dominguez et al., 1995. Proc. Natl. Acad. Sci. U.S.A. 92:8498–8502; Siegfried et al., 1994, Nature 367:76–80), is inhibited in Drosophila by zeste white 3/shaggy (zw3/sgg), the homolog of mammalian GSK-3. Although GSK-3$\mu$ was first described as an inhibitor of glycogen synthase (Woodgett, 1991, Trends Biochem. Sci. 16:177–181; Cohen et al., 1982, Eur. J. Biochem. 124:21–35), it also regulates distinct substrates in other signal transduction pathways, including the wnt pathway. A central role has also been demonstrated for the gene which encodes GSK-3β in the development of diverse organisms, including Dictyostelium and Xenopus (Harwood et al., 1995, Cell 80:139–48; Pierce et al., 1995, Development 121:755–765; He et al., 1995, Nature 374:617–622; Dominguez et al., 1995, Proc. Natl. Acad. Sci. U.S.A.

92:8498–8502). Therefore, assessment of whether lithium acts by inhibiting GSK-3β provides direct evidence for a relationship between this compound and wnt signaling.

In vitro Assay for GSK-3β Activity

Figure 2A:
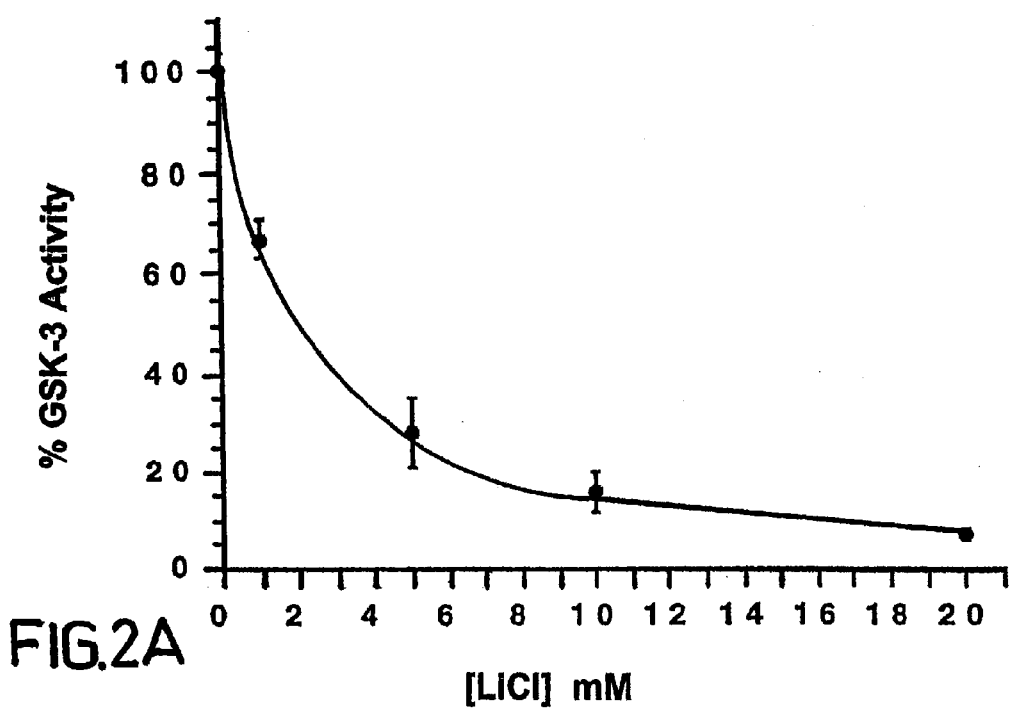
FIG. 2 is a pair of graphs which depict evidence of inhibition of GSK-3β by lithium in vitro. Panel A is a graph which depicts the activity of GSK-3β as a function of LiCl concentration. GSK-3β activity values are expressed as a percentage of GSK-3β activity as measured when LiCl was absent from the assay mixture. Purified GSK-3β was assayed as described in Example 1, and a peptide (GS-2) having a sequence derived from glycogen synthase was used as a substrate. Each data point represents the average of duplicate measurements from 3 independent experiments. Panel B is a graph which depicts the activity of GSK-3β in the presence of various salts. GSK-3β was assayed as described in Example 1. GSK-3β activity values are expressed as a percentage of GSK-3β activity, as measured when no salt solution was added to the standard assay mixture ("con" in the Figure). The GSK-3β activity values depicted in Panel B were measured in the presence of 20 mM of the particular salt indicated in the figure.
Figure 2B:
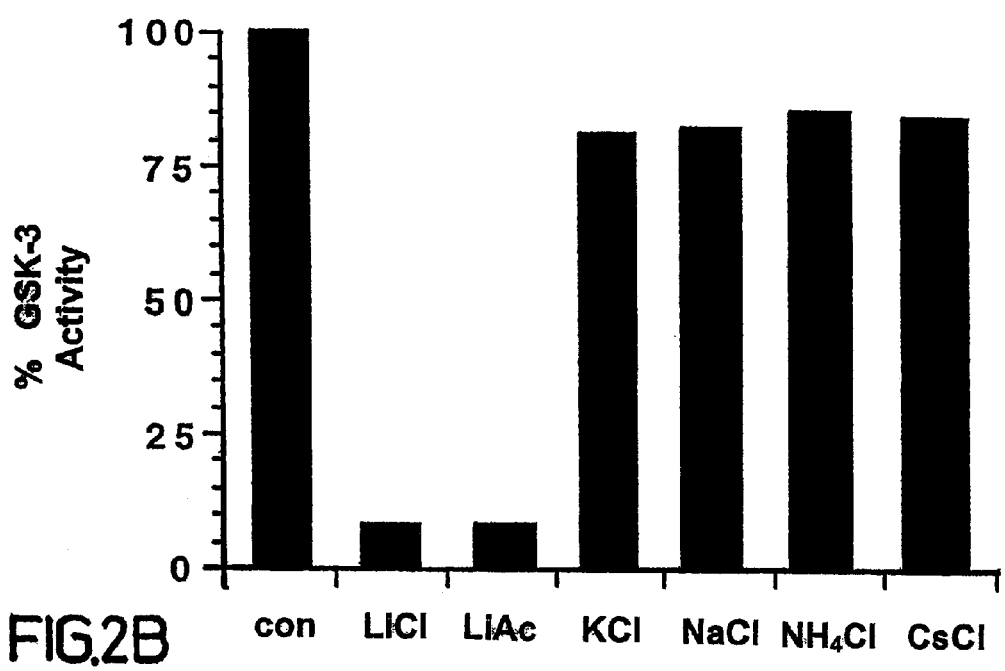
Figure 3A:
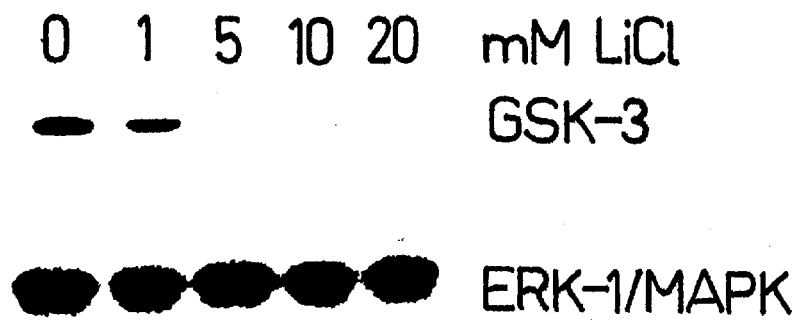
FIG. 3, comprises Panels A and B. Panel A is a pair of images of SDS-PAGE which depict detection of phosphorylated protein substrates following reaction of GSK-3β with protein phosphatase inhibitor-2 (I-2) or following reaction of ERK-1/MAP kinase with myelin basic protein (MBP). Reaction conditions are described in Example 1. Phosphorylated protein substrates were resolved by SDS-polyacrylamide gel electrophoresis and were visualized by autoradiography to detect $^{32}$P. Panel B is a graph which depicts the activities of GSK-3β, cAMP-dependent protein kinase A (PKA), ERK-1/MAP kinase, and casein kinase II (CKII). Each of the kinases was assayed as described in Example 1. The substrates used to assess GSK-3 activity were GS-2, I-2, and τ protein. The substrates used to assess the activities of ERK-1, PKA, and CKII were MBP, kemptide, and casein, respectively. Incorporation of $^{32}$P was measured as described in Example 1. The activity of each kinase was measured both in the assay mixture described in Example 1 (solid bars) and in the same assay mixture which further comprised 20 mM LiCl (striped bars). Kinase activity values are expressed as a percentage of the respective kinase activity, as measured when LiCl was not present in the standard assay mixture
Figure 3B:
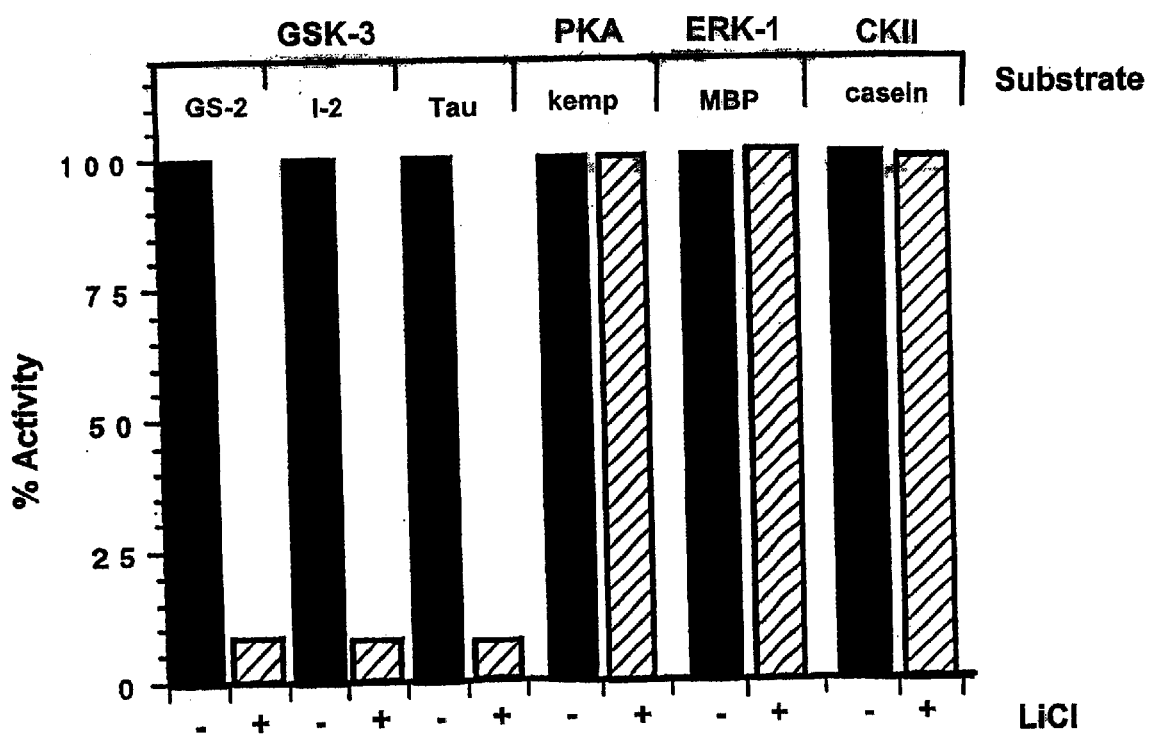

To determine whether a relationship exists between GSK-3β and wnt signaling, purified GSK-3β was assayed using a peptide substrate in a standard GSK-3β assay as described herein (Fiol et al., 1987, J. Biol. Chem. 262:14042–14048; Sutherland et al., 1993, Biochem. J. 296:15–19). The activity of GSK-3μ in this assay was inhibited by LiCl. The concentration of lithium which resulted in approximately 50% inhibition of GSK-3β activity was 2 mM (FIG. 2, Panel A) using the assay conditions described herein. Little inhibition of phosphorylation of peptide substrate by GSK-3μ was observed in the presence of NaCl, KCl, NH$_4$Cl, or CsCl, at a concentration of 20 mM each in the assay mixture (FIG. 2, Panel B). However, the addition of lithium acetate to the assay mixture resulted in a level of inhibition of GSK-3β activity which was nearly identical to that observed using LiCl (FIG. 2, Panel B). These results suggest that the inhibition of GSK-3β which was observed in these studies is mediated specifically by lithium cations, and not by other monovalent cations or by chloride. LiCl also inhibited GSK-3β-mediated phosphorylation of protein substrates, including I-2 (Hemmings et al., 1982, FEBS Lett. 150:319–324) and τ protein (Hanger et al., 1992, Neurosci. Lett. 147:58–62; Mandelkow et al., 1992, FEBS Lett. 314:315–321). The concentration of lithium which resulted in approximately 50% inhibition of GSK-3β phosphorylation of protein substrates was also near 2 mM (FIG. 3, Panel A). Furthermore, referring to the upper image in FIG. 3, Panel A, phosphorylated I-2 was detected when GSK-3β was reacted with I-2 in the absence of LiCl. Less phosphorylated I-2 was detected when 1 mM, 5 mM, or 10 mM LiCl was included in the assay mixture. Phosphorylated I-2 could not be detected when 20 mM LiCl was included in the assay mixture. In the lower image in FIG. 3, Panel A, phosphorylated MBP was detected following reaction of ERK-1/MAP kinase with MBP. The presence of 1, 5, 10, or 20 mM LiCl in the assay mixture had no effect on the amount of phosphorylated MBP which was detected. These results confirm that LiCl inhibits GSK-3β, but does not inhibit ERK-1/MAP kinase.

Significantly, inhibition of GSK-3β by lithium was observed at concentrations well within the therapeutic concentration range for lithium (0.5–1.5 mM) used for the treatment of mania. In Xenopus, the effective internal concentration after lithium treatment is not known precisely but reaches a maximum of approximately 8–9 mM (Busa, et al., 1989, Dev. Biol. 132:315–324).

The specificity of lithium inhibition of GSK-3β was further tested by assaying the activity of protein kinases other than GSK-3β, including PKA, ERK-1/MAP kinase, and CKII in the presence of lithium. When the concentration of lithium in the assay mixture was 20 mM, no inhibition of PKA activity was observed when either kemptide was used as a substrate (FIG. 3, Panel B) or casein was used. Similarly, minimal inhibition of ERK-1/ MAP kinase-mediated phosphorylation of MBP and minimal inhibition of CKII-mediated phosphorylation of casein was observed when 20 mM lithium was included in each of the assay mixtures (FIG. 3, Panels A and B). The absence of inhibition by lithium of protein kinases other than GSK-3β indicates that lithium is not a general inhibitor of protein kinases at a lithium concentration of approximately 20 mM. Rather, at this concentration, lithium is a specific inhibitor of GSK-3β.

Figure 4:
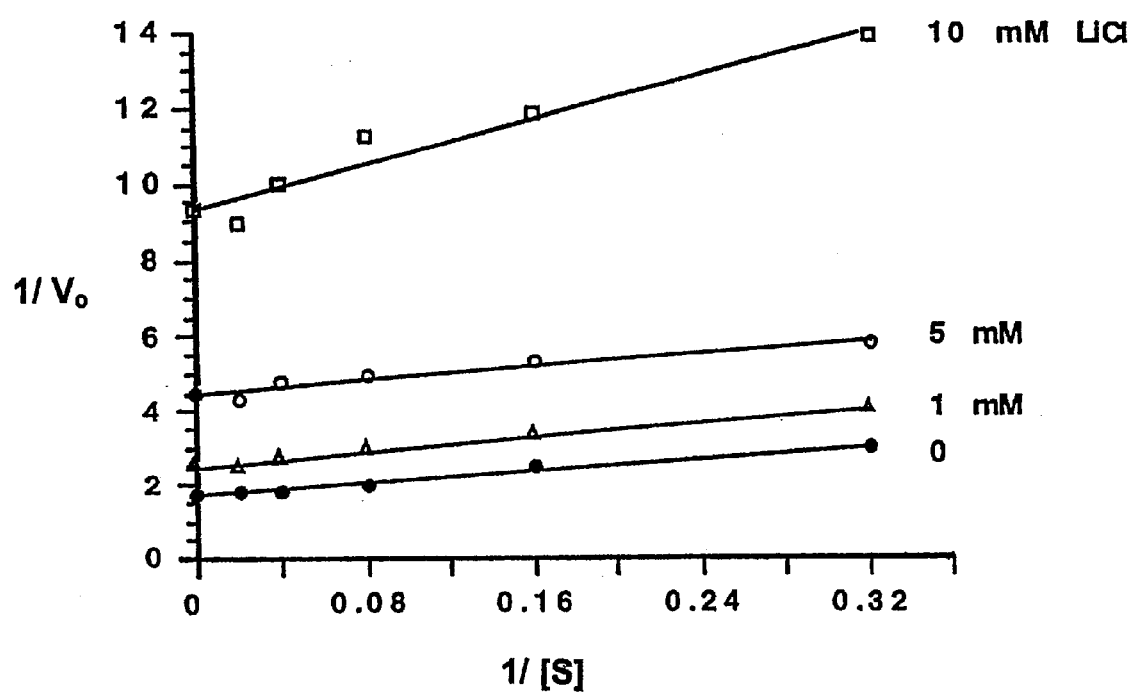
FIG. 4 is a double-reciprocal plot of initial velocity measurements of GSK-3β activity. GS-2 was used as the substrate, and GSK-3β activity was measured in the assay mixture described in Example 1, which further comprised a pre-determined concentration of LiCl. GSK-3β activity was measured in the presence of 3.125, 6.25, 12.5, 25, and 50 μM GS-2 peptide and 0, 1, 5, and 10 mM LiCl. An apparent maximum velocity corresponding to each LiCl concentration was calculated by extrapolation (i.e. extrapolated to 1/[S]=0) of a line fitted to the data obtained at the LiCl concentration. A plot of the inverse of the apparent maximum velocity corresponding to each LiCl concentration as a function of LiCl concentration established that the value of the inhibition constant ($K_i$) for LiCl was 2.1±0.6 mM. Initial reaction velocity was constant for up to 8 minutes. GSK-3β activity measurements were made 5 minutes after each reaction was initiated. The experiment was repeated 4 times with similar results. Kinetic analysis in this experiment may be complicated by the fact that GS-2 contains multiple GSK-3 p phosphorylation sites having different rates of phosphorylation (Fiol et al., 1990, J. Biol. Chem. 265:6061–6065).

The kinetic nature of the inhibition of GSK-3β by lithium was determined by measuring the initial velocity of the phosphorylation reaction catalyzed by GSK-3β. Multiple sets of GSK-3β activity assays were performed. In each set of assays, either the concentration of the substrate for GSK-3β or the concentration of LiCl was varied, while all other variables were maintained at constant values. The results of these sets of assays are presented as a double-reciprocal plot (FIG. 4). The data indicate that lithium acts as an uncompetitive inhibitor for GSK-3β ($K_i$ for LiCl=2.1 mM±0.6 mM; Smith et al., 1983, Principles of Biochemistry, McGraw-Hill, New York, 194–198). Because lithium is an uncompetitive inhibitor of GSK-3β, inhibition of GSK-3β by lithium cannot be overcome by increasing the concentration of the substrate of GSK-3β.

The inhibition of IMPase by lithium is also uncompetitive ($K_i$=0.8 mM). The ability of lithium to inhibit GSK-3β and IMPase in an uncompetitve fashion is an important feature for its therapeutic utility (Berridge et al., 1989, Cell 59:411–419; Hallcher et al., 1980, J. Biol. Chem. 255:10896–10901), since the degree of inhibition by lithium is proportional to the concentration of either enzyme's substrate.

The discovery that GSK-3β is the endogenous target of lithium action is supported by genetic data as well as by in vivo biochemical data. Inhibition of GSK-3β activity, achieved by expressing a dominant negative mutant of the gene encoding GSK-3β (DN-GSK-3β), results in dorsalization of Xenopus embryos. This dorsalization is similar to the dorsalization which results from lithium treatment of Xenopus embryos (Kao, et al., 1986, Nature 322:371–373; Pierce et al., 1995, Development 121:755–765; He et al., 1995, Nature 374:617–622; Dominguez et al., 1995, Proc. Natl. Acad. Sci. U.S.A. 92:8498–8502). The similarity of these results is consistent with the notion that lithium inhibits GSK-3β. In addition, disruption of the gene which encodes GSK-3β in Dictyostelium (gskA) induces cells which are normally fated to form spores to adopt the stalk-cell lineage (Harwood et al., 1995, Cell 80:139–48). This phenotype in Dictyostelium is duplicated by lithium treatment (Maeda, 1970, Dev. Growth and Differ. 12:217–227).

GSK-3β was first identified in mammals as the protein kinase responsible for the inhibitory phosphorylation of glycogen synthase (Woodgett, 1991, Trends Biochem. Sci. 16:177–181; Cohen et al., 1982, Eur. J. Biochem. 124:21–35). Insulin is known to inhibit GSK-3β (Sutherland et al., 1993, Biochem. J. 296:15–19; Welsh et al., 1993, Biochem. J. 294:625–629), which leads to increased glycogen synthesis. Lithium mimics insulin action by stimulating glycogen synthesis (Bosch et al., 1986, J. Biol. Chem. 261:16927–16931), and while the actual mechanism by which this occurs has not been demonstrated, it is likely that lithium mimics insulin by inhibiting GSK-3β.

Inhibition of GSK-3β by lithium provides a simple explanation for the effects of lithium on diverse systems and permits specific predictions regarding lithium therapy. For example, wnt signaling has been proposed to act through inhibition of GSK-3β (zw3/sgg) in Drosophila (Siegfried et al.,1994, Nature 367:76–80) and in Xenopus. In organisms in which the wnt pathway is conserved, lithium treatment should mimic wnt signaling. This has been demonstrated in Xenopus and zebrafish. Wnt-4 has been shown to be required for the induction of mesenchymal condensation in the formation of renal epithelium in mouse, and ectopically expressed wnt-1 can also induce mesenchymal condensation (Stark et al., 1994, Nature 372:679–683; Herzlinger et al., 1994, Dev. Biol. 166:815–818). These effects of wnt genes can be reproduced ex vivo by treating explanted renal mesenchyme with lithium which induces mesenchymal condensation in the explanted tissue (Davies et al., 1995, Dev. Biol. 167:50–60). Furthermore, wnt genes were first identified in mammals on account of their ability to stimulate cell division and to induce tumors in mammary cells (Nusse et al., 1984, Nature 307:131–136). Lithium can also stimulate cell division in primary mammary cell lines (Ptashne et al., 1980, J. Cell Physiol. 103:41–46). The mechanism by which lithium exerts these effects in renal mesenchyme and mammary cell lines has not been identified, but the correlation with wnt gene function is compelling given the phenotypic similarities resulting from lithium treatment and from wnt gene expression.

Lithium has effects on numerous other organisms and it may have multiple physiological targets. The data provided herein suggest that GSK-3β, which is abundantly expressed in brain (Woodgett, 1990, EMBO J. 9:2431–2438), may serve a role in signal transduction in the brain. Lithium inhibition of this signal transduction in the brain may explain the efficacy of lithium for the treatment of mania.

The results of the experiments presented in Example 1 establish that lithium inhibits the activity of GSK-3 in vitro. In Example 2, the results of studies of the inhibition of GSK-3 activity by lithium in vivo are presented.

EXAMPLE 2

Inhibition of GSK-3 in vivo: A Molecular Mechanism for Lithium Action

The materials and methods used in the experiments described in Example 2 are now described.

Materials used in this Study

Purified, bacterially-expressed GSK-3β was purchased from New England Biolabs. β-catenin protein from *Xenopus laevis*, a plasmid comprising a sequence encoding β-catenin protein (a sequence encoding Xenopus β-catenin in pCS2MT), and an antibody which specifically recognizes β-catenin protein were obtained from Ursula Gluck and Barry Gumbiner (Memorial Sloan Kettering). The sequence encoding Xenopus β-catenin is available in GENBANK, and traditional molecular biology techniques may be used to construct various plasmids which can be used to express β-catenin. Plasmid XG73, comprising a sequence encoding Xenopus GSK-3β, and plasmid XG114, comprising a sequence encoding DN-GSK-3 have been previously described (Pierce et al., 1995, Development 121:755–765) and were kindly provided by David Kimelman (University of Washington).

The collagenase promoter-luciferase construct is described (Angel et al., 1991, Biochim. Biophys. Acta, 1072:129–157; Dong et al., 1996, J. Biol. Chem. 271:9942–9946). The collagenase promoter includes an AP-1 site. [$\gamma^{32}$P]-ATP was obtained from Amersham. Western analysis was performed using an Enhanced Chemiluminescence System (ECL, ® Amersham).

Oocytes, Embryos, and Microinjection.

Stage 6 Xenopus oocytes were obtained by collagenase treatment of excised ovaries as described (Smith et al., 1994, Methods Cell Biol, 36:45–58). Each oocyte was microinjected with 10 nl of a solution comprising mRNA. Oocytes were incubated overnight at 18° C. in OR2+medium comprising 82.5 mM NaCl, 2.5 mM KCl, 1.0 mM CaCl$_2$, 1.0 mM MgCl$_2$, 1.0 mM sodium phosphate, and 5.0 mM HEPES, pH 7.8. Following incubation, oocytes were injected with 10–20 nl of a solution comprising τ protein.

In experiments involving embryos, eggs were fertilized as described in Example 1. Following fertilization, eggs were cultured in 0.1×MMR at 16–23° C. to form embryos. Each embryo was transferred to a solution comprising 3% Ficoll in 0.5×MMR for microinjection. Following microinjection, each embryo was returned to 0.1×MMR.

mRNA specifying DN-GSK-3 was microinjected into the subequatorial region of a ventral-vegetal blastomere in an embryo at the 16-cell stage. A volume of either 5 nl or 10 nl was microinjected depending upon the concentration of mRNA in the solution being microinjected. The same procedure was used to microinject myo-inositol into an embryo. In most experiments, 10 embryos were harvested at stage 8 to assess the level of DN-GSK-3protein expressed from the injected mRNA, and the level of DN-GSK-3protein in other embryos was assessed at stage 30–35.

GSK-3 Assays

In vitro phosphorylation by GSK-3 was performed as described in Example 1, except that the assay mixture was incubated at 25° C. and bacterially expressed r protein (50 µg/ml) was used as the substrate for GSK-3. Samples of the assay mixture were withdrawn at 0, 5, 10, 15, 20, 25, and 30 minutes after the reaction was initiated. Following withdrawal, each sample was adjusted to Laemmli sample buffer (Laernmli et al., 1970, Nature 227:680) and was analyzed by polyacrylamide gel electrophoresis using a 7.5% (w/v) polyacrylamide gel in the presence of 0.1% (w/v) sodium dodecyl sulfate. Following electrophoresis, each gel was either fixed and dried for autoradiography or transferred to nitrocellulose for subsequent Western blotting (Towbin et al., 1979, Proc. Natl. Acad. Sci. U.S.A. 76:4350; Anderson et al., 1982, Electrophoresis 3:135).

To effect in vivo phosphorylation of τ protein by GSK-3β, the following procedure was used. Either 10 ng of mRNA encoding Xenopus GSK-3β or 10 ng of mRNA encoding Dictyostelium GSK-3β was microinjected into individual stage 6 oocytes. Oocytes were incubated in OR2+medium for 16 hours at 18° C. Following incubation, 10–20 ng of τ protein was microinjected into the oocyte, and the oocyte was incubated in OR2+medium for a pre-determined period at 23° C.

To effect in vivo phosphorylation of τ protein by GSK-3β in oocytes treated with lithium, the procedure used in the preceding paragraph was used with the following modifications. Individual oocytes to be treated with lithium were transferred to OR2+medium containing 20 mM LiCl for 10 minutes at 18° C. prior to microinjection of τ protein into the oocyte. Following microinjection of τ protein, the oocyte was incubated in OR2+medium containing 20 mM LiCl for a pre-determined period at 23° C.

To measure in vivo phosphorylation of τ protein by GSK-3β in oocytes, the following procedure was used. Ten oocytes were homogenized in 100 µl of τ lysis buffer comprising 100 mM Tris, pH 6.5, 0.5 mM MgCl$_2$, 1 mM EDTA, 1 M NaCl, 2 mM dithiothreitol, 50 mM NaF, and 0.1 mM NaVO$_4$. Homogenized, lysed oocytes were centrifuged at 20,000×g for 5 minutes at 4° C. Supernatants were adjusted to 1×Laemmli sample buffer and were then electrophoresed on a 7.5% (w/v) polyacrylamide gel in the presence of 0.1% (w/v) sodium dodecyl sulfate. Following transfer of the polyacrylarnide gel to nitrocellulose, Western blot analysis of the gel was performed using PHF-1 as primary antibody (Kosik et al., 1988, Neuron, 7, 817–825). Another pair of primary antibodies, T14/T46, which recognize all forms of τ protein was also used in the Western blot analysis (Kosik et al., 1988, supra).

β-Catenin Stabilization in Oocytes.

The following experiments were performed to determine whether lithium stabilizes β-catenin in Xenopus oocytes. Oocytes were each microinjected with 7 ng of β-catenin protein. The oocytes were incubated for up to 6 hours at 18° C. either in OR2+medium or in OR2+medium containing 20 mM LiCl. Ten oocytes were homogenized in 100 µl of oocyte lysis buffer comprising 20 mM Tris-Cl pH 7.5, 150 mM NaCl, 1 mM EDTA, 1 mM PMSF, 0.1% (v/v) of a 10 µg/ml leupeptin solution, and 0.1% (v/v) of a 10 µg/ml aprotinin solution. Homogenized, lysed oocytes were centrifuged and electrophoresed as described herein. Western blot analysis was performed using an antibody that specifically recognizes β-catenin.

In another experiment, oocytes were individually injected with 5 ng of mRNA specifying β-catenin. Some of the oocytes were also injected with 5 ng of mRNA specifying Xenopus DN-GSK-3 or with 5 ng of mRNA specifying Xenopus GSK-3. The oocytes were incubated overnight at 18° C. in OR2+medium. One set of oocytes, into which neither DN-GSK-3 mRNA nor GSK-3 mRNA had been injected, was incubated overnight at 18° C. in OR2+medium which contained 20 mM LiCl. Ten oocytes were homogenized in 100 µl of oocyte lysis buffer. Homogenized, lysed oocytes were centrifuged and electrophoresed as described above. Western blot analysis was performed using an antibody that specifically recognizes β-catenin.

In yet another experiment, 7 ng of β-catenin protein was injected into the marginal zone of individual Xenopus embryos which were at the late 2 cell stage. The embryos were incubated in 0.1×MMR medium until they reached the 4 cell stage. At that point, a group of the embryos were treated with 0.3 M LiCl for 6 minutes and that group of embryos was transferred to 0.1×MMR medium containing 20 nM LiCl. A control group of embryos was not exposed to LiCl. Both groups of embryos were lysed, centrifuged, and electrophoresed according to the procedures described above for oocytes. Western blot analysis was performed using an antibody that specifically recognizes β-catenin.

c-Jun Activity in Xenopus Embryos

One-cell Xenopus embryos were microinjected with a solution comprising 100 pg of a supercoiled plasmid (AP1-luc) comprising the collagenase promoter, including an AP-1 site, fused to the luciferase coding region (Angel et al., 1991, Biochim. Biophys. Acta 1072:129–157). Following microinjection of AP1-luc, each embryo was incubated in a solution comprising 0.1×MMR medium and LiCl at a concentration of 0, 5, 10, or 20 mM. Other one-cell embryos were injected with a solution comprising 100 pg of a supercoiled plasmid (SV40-luc) which comprised the SV40 promoter sequence fused to the luciferase coding region. Following microinjection of SV40-luc, each of these embryos was incubated in a solution which comprised 0.1×MMR medium and LiCl at a concentration of 0, 5, 10, or 20 mM.

When the embryos reached developmental stage 12, the stage at which endogenous c-Jun protein is first expyessed (Dong et al., 1996, J. Biol. Chem., 271:9942–9946), ten embryos which had been microinjected with AP1-luc were harvested, as were ten embryos which had been microinjected with SV40-luc. Each group of ten- embryos was pooled and prepared for luciferase assays using the Promega Luciferase Assay System (Promega Corp., Madison, Wis.) according to the manufacturer's protocol, which was provided with the system. Light output, as a measure of luc gene expression in the embryos, was measured in a scintillation counter.

The results of the experiments described in Example 2 are now presented.

Assessment of GSK-3 -P Activity in Xenopus Oocytes

In order to study GSK-3 activity within the cellular milieu, an assay system using GSK-3 expression in Xenopus oocytes was used. τ protein, a microtubule-associated protein expressed in mammalian brain, was chosen as a substrate for GSK-3β. τ protein is the principal component of the paired helical filaments and neurofibrillary tangles found in patients afflicted with Alzheimer's disease (Mandelkow et al., 1997, TIBS 18:480–483). r protein is a substrate for GSK-3β, and is also a substrate for a number of other kinases, including ERK-1/MAP kinase, PKA, and cyclin-dependent kinase-5 (Lee, 1995, Curr. Op. Neurobiol. 5:663–668; Mandelkow et al., 1993, Trends Biol. Sci. 18:480–483). A panel of antibodies that recognize only specific, phosphorylated epitopes of τ protein has been generated (Lovestone et al., 1994, Curr. Biol. 4:1077–1086; Otvos et al., 1994, J. Neurosci. Res. 39:669–673). This panel includes at least one antibody, PHF-1, which recognizes a site on τ protein following phosphorylation thereof by GSK-3β. Thus, τ protein is a particularly advantageous substrate for use in the present invention because it is not normally expressed in oocytes and because phosphorylation of specific sites can be readily detected by Western blot analysis using antibodies which recognize a site on τ protein following phosphorylation thereof by GSK-3β.

The results of the experiments performed establish that τ protein phosphorylation occurs within a reasonable time frame in vitro and in vivo in Xenopus oocytes expressing GSK-3β. τ protein phosphorylation by GSK-3 has been demonstrated by several groups of investigators (Hanger et al., 1992, Neurosci. Lett. 147, 58–62; Mandelkow et al., 1992, FEBS Lett. 314:315–321; Mulot et al., 1994, FEBS Lett., 349:359–364). However, the analytical methods used by these groups are unwieldy, requiring that GSK-3β and τ protein be incubated for between 30 minutes to 24 hours. Studies which require co-expression of GSK-3β and τ protein in cell lines involve even longer incubation periods. As disclosed herein, GSK-3β is capable of phosphorylating τ protein within 5 minutes, both in vitro and in vivo. As indicated in the images in FIG. 5, Panels A and B, in vitro phosphorylation of τ protein is evident after only 5 minutes of incubation of τ protein with GSK-3β.

To assess GSK-3 activity within oocytes in vivo, bacterially-expressed τ protein was microinjected into stage 6 Xenopus oocytes, which were then incubated for a preselected period ranging from 5 minutes to 6 hours post-τ-injection. Following incubation, the oocytes were lysed, and protein obtained therefrom was electrophoresed and subjected to Western blot analysis using either PHF-1 antibody or T14/T46 antibodies.

No signal was detected when PHF-1 antibody was used (FIG. 5, Panel B), which suggests that serines 396 and 404 on τ protein are not phosphorylated under these conditions. This observation is consistent with a low level of endogenous GSK-3 activity in Xenopus oocytes. After prolonged incubation, some forms of τ protein having altered electrophoretic mobility were detected (FIG. 5, Panel B, lanes 3, 4, and 5), which may indicate phosphorylation of τ protein by protein kinases present in the oocytes.

Figure 5A:
FIG. 5 is a series of images of Western blots which depict in vitro and in vivo phosphorylation of r protein by GSK-3β. Panel A is a pair of images of Western blots which depict in vitro phosphorylation of τ protein by GSK-3β. Purified GSK-3β was incubated with [γ$^{32}$P]-ATP in the presence of τ protein. At the time indicated in the Panel A, the reaction was stopped by the addition of Laemmli sample buffer, and the assay mixture was subjected to SDS-polyacrylamide gel electrophoresis. In the upper image, $^{32}$P uptake was detected by autoradiography. $^{32}$P incorporation was detected following 5 minutes of incubation (lane 2) and was observed to increase as the incubation time increased. In the lower image, phosphorylated τ protein was detected by immunostaining with PHF-1, an antibody specific for τ protein which is phosphorylated at serine residues 396 and 404. The presence of phosphorylated τ protein, as assessed by PHF-1 immunostaining, was detected following 5 minutes of incubation (lane 2) and was observed to increase as the incubation time increased. Panel B is a pair of images of Western blots which depict in vivo phosphorylation of τ protein by GSK-3β. Stage 6 Xenopus laevis oocytes were injected with mRNA specifying GSK-3β, and were later injected with τ protein. Oocytes which were not injected with GSK-3β-specific mRNA served as a control. Following incubation for the time indicated in the Figure, oocytes were harvested, lysed, and the lysate was subjected to SDS-polyacrylamide gel electrophoresis. Western blot analysis was performed, using PHF-1 antibody or using antibodies T14/T46, which recognize both phosphorylated and non-phosphorylated forms of τ protein.
Figure 5B:
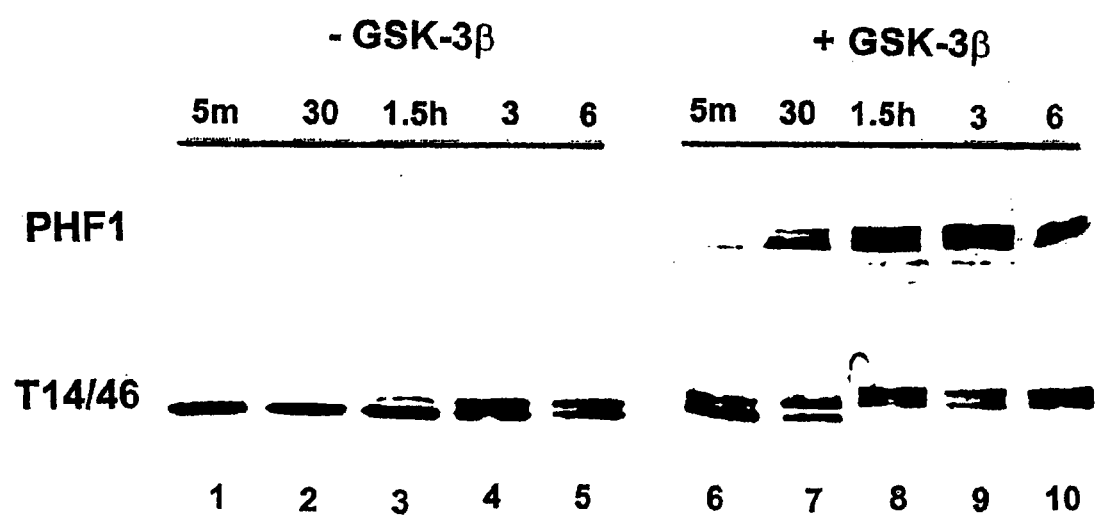

GSK-3β was expressed in oocytes microinjected with MRNA specifying Xenopus GSK-3β (Pierce et al., 1995, Development 121:755–765). Sixteen hours following microinjection of GSK-3β mRNA, τ protein was microinjected into the oocytes. Following microinjection of τ protein, oocytes were harvested after selected periods of time. The harvested oocytes were lysed, electrophoresed, and subjected to Western blot analysis as described.

τ protein which was microinjected into Xenopus oocytes was rapidly phosphorylated by GSK-3β (i.e. within 5 minutes post-τ-injection), the GSK-3β being expressed in the oocytes following microinjection thereof with mRNA specifying GSK-3β. The rapid phosphorylation of τ protein is depicted in FIG. 5, Panel B, by immunoreactivity of PHF-1 antibody with τ protein from harvested oocytes which expressed GSK-3β. The results presented in FIG. 5, Panel B also establish that GSK-3β-mediated phosphorylation of τ protein persists for up to 6 hours (lane 10). The level of τ protein in the oocytes did not change significantly over this time period. There was a decrease over time in the electrophoretic mobility of τ protein which had been phosphorylated by GSK-3β, as determined by Western blot analysis using antibodies indifferent to the phosphorylation state of τ protein. The decrease in mobility may be explained by the increased phosphorylation of τ protein by GSK-3 in addition to endogenous kinases in Xenopus oocytes.

Approximately equal immunostaining of all lanes in FIG. 5, Panel B using T14/T46 antibody confirmed that approximately equal amounts of τ protein were included in all assay mixtures.

These results establish that the activity of expressed GSK-3β may be readily measured in oocytes without the interference usually observed in mammalian cells which results from the high background phosphorylation of substrate, which is presumably caused by protein kinases other than GSK-3 (Sperber et al., 1995, Neurosci. Lett. 197:149–153).

Western blot analysis of extracts from oocytes which were injected with mRNA specifying GSK-3β using an antibody which recognizes GSK-3 indicated that GSK-3 protein was present at an approximately constant level throughout the assay. Western blot analysis of extracts from oocytes which were not injected with mRNA specifying GSK-3 did not detect endogenous GSK-3.

The Effect of Lithium on GSK-3β Activity in vivo

In order to test whether lithium inhibits Xenopus GSK-3 in vivo, the effect of lithium on the activity of GSK-3β was investigated using the oocyte assay system described above. Oocytes were injected with MRNA specifying GSK-3β as described herein, incubated for 16 hours, and then transferred either to medium containing no LiCl or to medium containing 20 mM LiCl. τ protein was injected, oocytes were incubated for an additional 2 hours, and then oocytes were harvested for Western blot analysis as described. The results of these experiments are depicted in FIG. 6. In FIG. 6, Panel A, PHF-1 immunoreactivity as a measure of GSK-3β activity, was observed only in oocytes expressing GSK-3β (compare lanes 2 and 3). In the presence of LiCl, the GSK-3β activity was markedly inhibited (FIG. 6, Panel A, lane 4).

In another experiment, τ protein and MRNA specifying GSK-3β were microinjected into oocytes and the oocytes were incubated in the presence of extracellular concentrations of LiCl ranging from 0 to 50 mM in separate assays. Oocytes were incubated, harvested, and lysed, and the lysate was electrophoresed as described herein. The results of this experiment are presented in FIG. 6, Panel C. Clear inhibition of phosphorylation of τ protein by GSK-3β was observed when the extracellular concentration of LiCl was 5 to 10 mM (FIG. 6, Panel C, lanes 2 and 3). PHF-1 immunoreactivity was nearly undetectable at 20 to 50 mM (FIG. 6, Panel C, lanes 4 and 5). It should be noted that, after a 4 hour incubation period of an embryo in LiCl, the intracellular concentration of lithium cation does not exceed 5% of the extracellular concentration (Breckenridge et al., 1987, Development 99:353–370). Thus, the intracellular concentrations of lithium cation in the experiments described herein are likely to be considerably lower than the extracellular concentrations of LiCl in the assay mixture.

The results presented herein establish that lithium inhibits Xenopus GSK-3β in vivo. This inhibition explains the dorsalizing effect of lithium on amphibian development. Lithium treatment also phenocopies the gsk4 mutation (i.e. loss of GSK-3 expression) in *Dictyostelium discoideum*, which leads to a failure to produce spores and an expansion of basal stalk cells.

To determine whether GSK-3β obtained from this primitive eukaryote is directly inhibited by lithium, gskA was subcloned into a Xenopus expression vector, pCS2+(Turner et al., 1994, Genes & Dev. 8:1434–1447). The protein encoded by gskA was expressed in Xenopus oocytes using standard molecular biology techniques (see, e.g. Sambrook, et al., 1989, In: Molecular Cloning: A Laboratory Manual, Cold Spring Harbor Laboratory, New York). As indicated by the results presented in FIG. 6, Panel A, Dictyostelium GSK-3 (lane 5) phosphorylated τ protein at a level equal to the phosphorylation catalyzed by GSK-3β obtained from Xenopus (lane 3). Dictyostelium GSK-3 activity was inhibited by lithium (FIG. 6, Panel A, lane 6). As demonstrated by the results presented in FIG. 6, Panel B, approximately equal amounts of GSK-3β protein were detected in oocytes incubated in the medium which contained LiCl and in oocytes incubated in the medium which contained no LiCl. These results confirm that LiCl inhibits the activity of GSK-3β rather than the translation of mRNA specifying GSK-3β.

These results establish that lithium inhibits the Dictyostelium homolog of GSK-3 to the same extent that lithium inhibits the Xenopus homolog. Therefore, it should be expected that lithium will inhibit GSK-3β enzymes across a broad portion of the phylogenetic spectrum.

Activation of the wnt Signaling Pathway in Xenopus by Lithium Genetic epistasis experiments in Drosophila suggested that zeste-white-3/shaggy (zw3/sgg), the Drosophila homolog of GSK-3β, is inhibited by wnt signaling. This suggestion has been confirmed biochemically (Cook et al., 1996, EMBO J. 15:4526–4536). One consequence of GSK-3β inhibition in Drosophila and in Xenopus is an accumulation, due to protein stabilization, of β-catenin protein in the responding cells (i.e. the armadillo phenotype in Drosophila; Miller et al., 1996, Genes & Dev. 10:2527–2539). β-Catenin is essential for dorsal axis formation in Xenopus embryos (Heasman et al., 1994, Cell 79:791–803) and also appears to be stabilized by inhibition of Xenopus GSK-3β activity (Yost et al., 1996, Genes & Dev. 10:1443–1454). Thus, activation of the wnt signaling pathway involves stabilization of β-catenin in vertebrates and invertebrates, which presumably acts through inhibition of GSK-3β.

In order to observe activation of the wnt pathway in oocytes and embryos, β-catenin stabilization was assessed, as described in the case of Drosophila (van Leeuwen, et al., 1994, Nature 368:342–344) and Xenopus (Yost et al., 1996, Genes & Dev. 10:1443–1454). mRNA specifying β-catenin was injected into oocytes and MRNA specifying either wild-type or DN-GSK-3 was also injected into the oocytes. DN-GSK-3 has previously been shown to mimic activation of the wnt pathway in Xenopus embryos and has recently been shown to lead to stabilization of β-catenin in Xenopus embryos (Yost et al., 1996, Genes & Dev. 10:1443–1454). The experiments described herein establish that expression of DN-GSK-3 also leads to accumulation of β-catenin in Xenopus oocytes (FIG. 7, Panel A, lane 3). Expression of wild-type GSK-3 had no apparent effect on β-catenin accumulation in oocytes (FIG. 7, Panel A, compare lanes 1 and 4), which suggests that the level of GSK-3 activity is not a limiting factor in the endogenous accumulation of β-catenin in Xenopus oocytes.

The data presented in Example 2 indicate that GSK-3 activity is endogenous in oocytes and can be monitored by following β-catenin turnover. To address whether lithium inhibits endogenous oocyte GSK-3, oocytes which were injected with β-catenin specific MRNA were cultured in medium containing 20 mM LiCl. As indicated by the results presented in lane 2 of FIG. 7, Panel A, lithium leads to accumulation of β-catenin to an extent comparable to the accumulation observed in cells microinjected with DN-GSK-3 (lane 3). This observation suggests that lithium activates the wnt signaling pathway through inhibition of endogenous GSK-3.

In order to demonstrate that β-catenin accumulation is a caused by stabilization of pre-existing β-catenin protein rather than by increased β-catenin protein synthesis, an additional experiment was performed. Purified, recombinant β-catenin protein was injected into stage 6 oocytes, which were then cultured either in buffer containing no LiCl or in buffer containing 20 mM LiCl. Oocytes were harvested, lysed, and electrophoresed as described herein. Western blot analysis using an antibody that specifically recognizes β-catenin established that the level of injected β-catenin protein fell in oocytes which were not treated with LiCl. The approximate half-life of β-catenin in these oocytes was 1 hour. β-Catenin protein is almost undetectable in the absence of LiCl at 4 and 6 hours post-injection (FIG. 7, Panel B, lanes 4– and 6–). Western blot analysis using an antibody that specifically recognizes β-catenin established that injected β-catenin protein persisted in oocytes treated with LiCl (FIG. 7, Panel B, lanes 4+and 6+). Stabilization of β-catenin protein by lithium was found to continue for at least 18 hours post-injection.

Endogenous β-catenin was present at much lower levels in oocytes than levels of β-catenin obtained following microinjection of β-catenin specific mRNA into oocytes. Endogenous β-catenin was not readily detected using the conditions described (FIG. 7, Panel B, lane 1). However, recombinant β-catenin contains several copies of the myc epitope at the carboxyl terminus, which causes the protein to migrate more slowly during SDS-polyacrylamide gel electrophoresis than does endogenous β-catenin. Thus, injected β-catenin protein can be readily distinguished from endogenous β-catenin protein. The possibility that the protein levels observed in the presence of LiCl represent increased protein synthesis was therefore eliminated. For these reasons, these results establish that lithium stabilizes β-catenin protein in Xenopus oocytes.

To confirm this observation, β-catenin protein was injected into the marginal zone of late 2 cell embryos. At the four-cell stage, embryos were treated with LiCl as described herein. Treated and non-treated embryos were harvested, lysed, electrophoresed, and subjected to Western blot analysis as described herein. Lithium induced stabilization of β-catenin protein injected into the embryos (FIG. 7, Panel C, compare lanes 4– and 4+). The stabilization of β-catenin protein which was observed following lithium treatment was similar to the effect of DN-GSK-3 (Yost et al., 1996, Genes & Dev. 10:1443–1454) and is consistent with activation of the wnt pathway.

A higher level of endogenous β-catenin was observed in Xenopus embryos (FIG. 7, Panel C, lane 1) than was observed in oocytes (compare lane 1 in FIG. 7, Panel B with lane 1 in FIG. 7, Panel C). The level of endogenous β-catenin observed in Xenopus embryos did not appear to change significantly in response to lithium, most likely because the majority of the endogenous protein is associated with cadherin and is therefore not accessible to regulation by the wnt pathway (Fagatto et al., 1994, Development 120:3667–3679; Yost et al., 1996, Genes & Dev. 10:1443–1454; Schneider et al., 1996, Mechanisms Dev. 57:191–198).

Activation of AP-1 by lithium

The transcription factor, c-Jun, has been demonstrated to be a substrate for GSK-3 both in vitro and in cell lines overexpressing GSK-3 and c-Jun. GSK-3 phosphorylates c-Jun at three amino acids, specifically Thr-239, Ser-243, and Ser-249 near the DNA binding domain of c-Jun. Phosphorylation of c-Jun at these amino acid positions inhibits DNA binding which, in turn, inhibits c-Jun activity (Boyle et al., 1991, Cell 64:573–584; Plyte et al., 1992, Biochim. Biophys. Acta 1114:147–162). In order to determine whether lithium induces activation of endogenous c-Jun by inhibiting GSK-3 in Xenopus embryos, the following experiments were performed.

Embryos were injected at the 1 cell stage with the plasmid AP1-luc or the plasmid SV40-luc. Injected embryos were cultured as described herein, in a medium containing a pre-determined concentration of LiCl. Embryos were harvested and lysed, and luciferase activity in each embryo lysate was determined. Lysates from embryos which were injected with AP1-luc and were cultured in medium which contained no LiCl expressed a low level of luc activity. However, when LiCl was present in the incubation medium, luciferase activity was increased more than 20-fold in the embryo lysates (FIG. 8, Panel A). These results are consistent with inhibition of GSK-3 by lithium which in turn prevents GSK-3 from phosphorylating c-Jun thereby facilitating enhancement of transcription of the luciferase coding region of plasmnid AP1-luc by c-Jun. An increase in AP-1 complex formation was observed in polyacrylamide gel electrophoresis retardation assays, and corresponded with the presence of LiCl in the incubation medium.

To confirm that the increase in luc expression was effected by enhanced c-Jun activation, the experiment was repeated using a plasmid having an SV40 promoter which, because it does not contain an AP-1 site, it is not affected by c-Jun activity. Transcription of luc which is initiated at the SV40 promoter should, therefore, be unaffected by alteration of c-Jun activity. Injection of the plasmid SV40-luc into Xenopus oocytes yielded a high level of luciferase expression which was not affected by the presence of lithium in the incubation medium (FIG. 8, Panel B). Gene expression driven by the SV40 promoter was detectable much earlier than gene expression which was driven by the AP-1 site-containing collagenase promoter. Gene expression driven by the SV40 promoter began at the midblastula transition, while gene expression driven by the collagenase promoter began at stage 11 to 12. Luciferase expression driven by the SV40 promoter reached a level which was an order of magnitude higher than the level of luciferase expression driven by the collagenase/AP-1 promoter in injected embryos. The values presented in FIG. 8, Panel B are normalized to the maximum luciferase activity observed to be expressed from the respective promoters.

These results confirm that lithium enhances activation of endogenous c-Jun in embryos.

Myo-inositol blocks ectopic axis induced by DN-GSK-3

Lithium-induced dorsalization of Xenopus embryos can be blocked by coinjection of myo-inositol and lithium into embryos (Busa et al., 1989, Dev. Biol. 132:315–324). While this observation may be viewed to support the inositol depletion hypothesis, myo-inositol may also block dorsal axis induction by lithium via a more indirect mechanism which is independent of IMPase inhibition. The ability of myo-inositol to block dorsal axis formation which is induced by DN-GSK-3 was therefore investigated because DN-GSK-3 is not expected to act through depletion of myo-inositol.

DN-GSK-3-specific MRNA was injected together with water or with myo-inositol into a ventral-vegetal cell of 16-cell embryos. Embryos were incubated and examined at later stages for second axis formation. As indicated by the results presented in Table 1 and FIG. 9, coinjection of myo-inositol and DN-GSK-3 MRNA clearly reduced the frequency and the extent of second axis induction by DN-GSK-3. The embryo depicted in FIG. 9, Panel A exhibited induction of a complete second axis, having a cement gland, a head, and eyes. The embryo depicted in FIG. 9, Panel B exhibited induction of an incomplete secondary axis, which lacked clear head structures. The most striking effect was observed to be on the anterior extent of the ectopic axes that form after coinjection of myo-inositol and DN-GSK-3 mRNA. Even where anterior structures such as cement gland are present in embryos injected with myo-inositol, they are markedly reduced in size, compared to those present in embryos which were not injected with myo-inositol (as indicated in Table 1). Myo-inositol did not inhibit the synthesis of DN-GSK-3protein and had no discernible effect on formation of the primary dorsal axis when injected into dorsal blastomeres (Busa et al., 1989, Dev. Biol. 132:315–324).

TABLE 1

The effect of injection of DN-GSK-3 or DN-GSK-3/myo-inositol into Xenopus embryos on second axis formation therein.

| Set | COMPLETE SECOND AXIS | | TOTAL WITH SECOND AXES | | |
|---|---|---|---|---|---|
| | DN-GSK-3 | DN-GSK-3 + myo-inositol | DN-GSK-3 | DN-GSK-3 + myo-inositol | Control |
| I | 8/19 | 0/19 | 12/19 | 7/19 | 0/19 |
| II | 8/23 | 1/24 | 14/23 | 9/24 | 0/24 |
| III | 8/15 | 4/15 | 10/15 | 7/15 | 0/15 |
| Total | 24/57* | 5/58* | 36/57* | 23/58* | 0 |
| % | 42 | 9 | 63 | 40 | 0 |

*The results obtained following injection of DN-GSK-3 and H$_2$O are significantly different from the results obtained following injection of DN-GSK-3 + myo-inositol in both formation of complete second axis and formation of total second axis, having a value of $p < 0.05$, as determined by Waller-Duncan statistical analysis.

In summary, the results presented herein establish that lithium treatment stimulates the wnt signaling pathway, glycogen synthesis, and, in Dictyostelium, stalk cell specification. These results are consistent with direct inhibition of GSK-3 by lithium. Furthermore, lithium treatment stimulates AP-1 directed transcription, which is also consistent with inhibition of GSK-3 by lithium. The data presented herein also establish in vivo inhibition of GSK-3 by lithium. Consequently, administration of lithium to an animal, or of another inhibitor of GSK-3, can be used to activate wnt signaling, enhance glycogen synthesis (in place of, or in addition to, insulin), alter cell differentiation, and increase transcription enhancement mediated by c-Jun.

Both vertebrate (Xenopus as well as mammalian) and invertebrate (Dictyostelium and Drosophila) forms of GSK-3 are inhibited by lithium, which indicates that the sensitivity of GSK-3 to lithium is conserved across a broad phylogenetic spectrum. These data support the hypothesis that inhibition of GSK-3 is a general mechanism for lithium action in these settings and are consistent with the result presented in Example 1, namely that purified GSK-3 is inhibited by lithium in vitro. Furthermore, the results presented herein establish that lithium or another GSK-3 inhibitor, will be effective across a broad phylogenetic spectrum to activate wnt signaling, enhance glycogen synthesis, alter cell differentiation, and increase transcription enhancement mediated by c-Jun.

EXAMPLE 3

Identification of Ro31-8220 as a GSK-3 Inhibitor

In order to determine screen a test compound to determine whether that test compound is a GSK-3 inhibitor, the following experiments were performed. A bisphosphonate compound denoted Ro31-8220 (Calbiochem, La Jolla, Calif.) was used as the test compound. The assays described in Example 1 were performed. Ro31-8220 was added to the assay mixture to achieve predetermined concentrations. Ro31-8220 concentrations in the range from 0 to 10 $\mu$M were tested. Approximately 50% inhibition of GSK-3$\beta$ activity was observed when the concentration of Ro31-8220 in the assay mixture was 40 nM. These results indicate that Ro31-8220 is an inhibitor of GSK-3.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention.

What is claimed is:

1. A method of treating a GSK-3 related disorder other than Alzheimer's disease in an animal comprising administering to said animal a GSK-3 inhibitor suspended in a pharmaceutically acceptable carrier, wherein said GSK-3 inhibitor is not lithium and is identified by:

(a) providing a mixture comprising GSK-3, a source of phosphate, a GSK-3 substrate, and a GSK-3 assay buffer;

(b) incubating said mixture in the presence or absence of a test compound;

(c) measuring the level of phosphorylation of said GSK-3 substrate; and (d) determining whether the level of phosphorylation of said GSK-3 substrate is lower in the presence of said test compound than in the absence of said test compound, and further wherein the GSK-3 related disorder is selected from the group consisting of bipolar disorder, mania, and leukopenia.

* * * * *

SEQUENCE LISTING

<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence:GSK-3(beta) substrate

<400> SEQUENCE: 1

Arg Pro Ala Ser Tyr Pro Pro Ser Pro Ser Leu Ser Arg His Ser Ser
 1               5                  10                  15

-continued

```
Pro His Gln Ser Pro Glu Asp Glu Glu Glu
            20                  25
```